(12) United States Patent
Okano

(10) Patent No.: US 9,943,254 B2
(45) Date of Patent: Apr. 17, 2018

(54) BIOLOGICAL COMPONENT ESTIMATING APPARATUS, BIOLOGICAL COMPONENT ESTIMATING METHOD, AND COMPUTER PROGRAM PRODUCT

(71) Applicant: Kabushiki Kaisha Toshiba, Minato-ku (JP)

(72) Inventor: Hideaki Okano, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 102 days.

(21) Appl. No.: 15/069,266

(22) Filed: Mar. 14, 2016

(65) Prior Publication Data

US 2016/0275677 A1    Sep. 22, 2016

(30) Foreign Application Priority Data

Mar. 20, 2015 (JP) ................. 2015-058581

(51) Int. Cl.
  *G06K 9/00* (2006.01)
  *A61B 5/1455* (2006.01)
  *A61B 5/145* (2006.01)
  *A61B 5/00* (2006.01)

(52) U.S. Cl.
  CPC ........ *A61B 5/1455* (2013.01); *A61B 5/14532* (2013.01); *A61B 5/70* (2013.01); *A61B 5/742* (2013.01)

(58) Field of Classification Search
  None
  See application file for complete search history.

(56) References Cited

U.S. PATENT DOCUMENTS

| 6,075,610 A | 6/2000 | Ueda et al. |
| 7,254,429 B2 | 8/2007 | Schurman et al. |
| 2011/0124988 A1 | 5/2011 | Cuccia |
| 2011/0157551 A1 | 6/2011 | Plamann et al. |
| 2016/0097716 A1* | 4/2016 | Gulati ............... A61B 5/02416 250/339.01 |

(Continued)

FOREIGN PATENT DOCUMENTS

| JP | 10-26585 A | 1/1998 |
| JP | 2000-507348 A | 6/2000 |

(Continued)

OTHER PUBLICATIONS

Katsuhiko Maruo, "Study of noninvasive blood glucose measurement by using near-infrared spectroscopy", Jun. 2007, 146 Pages (with English Abstract).

(Continued)

*Primary Examiner* — Weiwen Yang
(74) *Attorney, Agent, or Firm* — Oblon, McClelland, Maier & Neustadt, L.L.P.

(57) ABSTRACT

According to an embodiment, a biological component estimating apparatus includes a first acquiring unit and a first estimating unit. The first acquiring unit acquires a scattering coefficient distribution image having each pixel specified with a scattering coefficient of a measurement target region of a biological body for light including a wavelength range in a near infrared range. The first estimating unit estimates an amount of change in a biological component based on the scattering coefficient distribution image.

12 Claims, 13 Drawing Sheets

(56) References Cited

U.S. PATENT DOCUMENTS

2017/0135616 A1* 5/2017 Sato .................. A61B 5/14551

FOREIGN PATENT DOCUMENTS

| JP | 2012-502268 A | 1/2012 |
|----|---------------|--------|
| JP | 2014-18478 A | 2/2014 |
| WO | WO 97/35179 A1 | 9/1997 |

OTHER PUBLICATIONS

Veronika V. Sapozhnikova, et al., "Effect on blood glucose monitoring of skin pressure exerted by an optical coherence tomography probe" Journal of Biomedical Optics, vol. 13, 2008, pp. 021112-1-021112-4.

Kirill V Larin, et al., "Specificity of noninvasive blood glucose sensing using optical coherence tomography technique: a pilot study" Physics in Medicine and Biology, vol. 48(10), 2003, pp. 1371-1390.

Thomas D. O'Sullivan, et al., "Diffuse optical imaging using spatially and temporally modulated light" Journal of Biomedical Optics, vol. 17(7), 2012, pp. 071311-1-071311-14.

* cited by examiner

| USER ID | MEAS- URE- MENT ID | ACQUISI- TION TIMING | AMOUNT OF CHANGE IN BLOOD GLUCOSE LEVEL | TRACKING INFORMATION |||
|---|---|---|---|---|---|---|
| | | | | REFERENCE TEMPLATE | FIRST PATTERN | RELATIVE POSITION |
| A | 1 | 2015/3/01 09:00:00 | 2 | | | |
| | | 2015/3/01 09:10:00 | 1 | | | |
| | | 2015/3/01 09:20:00 | 4 | | | |
| | | 2015/3/01 09:30:00 | 1 | | | |
| | 2 | 2015/3/01 10:10:00 | 10 | | | |
| | | 2015/3/01 10:20:00 | 10 | | | |
| | | 2015/3/01 10:30:00 | 10 | | | |
| | | 2015/3/01 10:40:00 | 10 | | | |
| | | 2015/3/01 10:50:00 | 3 | | | |
| | | 2015/3/01 11:00:00 | 2 | | | |
| ... |||||||

FIG.2B

| FIRST TIME PERIOD | ABNORMAL AMOUNT OF CHANGE |
|---|---|
| | |
| | |

| AMOUNT OF CHANGE IN BLOOD GLUCOSE LEVEL | AMOUNT OF CHANGE IN SCATTERING COEFFICIENT |
|---|---|
| | |
| | |

34

40A (40)

40B (40)

42A (42)

42B (42)

44

46

US 9,943,254 B2

BIOLOGICAL COMPONENT ESTIMATING APPARATUS, BIOLOGICAL COMPONENT ESTIMATING METHOD, AND COMPUTER PROGRAM PRODUCT

CROSS-REFERENCE TO RELATED APPLICATION(S)

This application is based upon and claims the benefit of priority from Japanese Patent Application No. 2015-058581, filed on Mar. 20, 2015; the entire contents of which are incorporated herein by reference.

FIELD

An embodiment described herein relates generally to a biological component estimating apparatus, a biological component estimating method, and a computer program product.

BACKGROUND

For patients with diabetes or abnormal glucose tolerance, monitoring of the blood glucose level is indispensable. A representative method among the known methods for monitoring a blood glucose level is a method using a blood sample obtained from a biological body. The method involves reacting glucose in the blood sample with an enzyme such as glucose oxidase (GOD) or glucose dehydrogenase (GDH), for example. This process generates electrons corresponding to the amount of glucose in the blood. With this known method, a voltage is applied to the blood so as to use the resultant current level for monitoring the blood glucose level.

The amount of a biological component such as blood glucose may change successively in the biological body. In order to measure the amount of change in the biological component, it has been conventionally necessary to draw blood from the subject repeatedly by needling. From the viewpoint of pain reduction and infection prevention, for example, there has been a demand for a non-invasive approach for measuring a change in the blood glucose level. Known non-invasive approaches for measuring a change in the blood glucose level include a technology for estimating the blood glucose level using the absorbance spectrum of skin, and a technology for estimating the blood glucose level using a tomographic image obtained with optical coherence tomography (OCT).

BRIEF DESCRIPTION OF THE DRAWINGS

FIGS. 2A, 2B, and 2C are schematics for illustrating exemplary data structures of first information, second information, and third information, respectively;

DETAILED DESCRIPTION

According to an embodiment, a biological component estimating apparatus includes a first acquiring unit and a first estimating unit. The first acquiring unit acquires a scattering coefficient distribution image having each pixel specified with a scattering coefficient of a measurement target region of a biological body for light including a wavelength range in a near infrared range. The first estimating unit estimates an amount of change in a biological component based on the scattering coefficient distribution image.

An embodiment will now be explained in detail with reference to the appended drawings.

Figure 1:
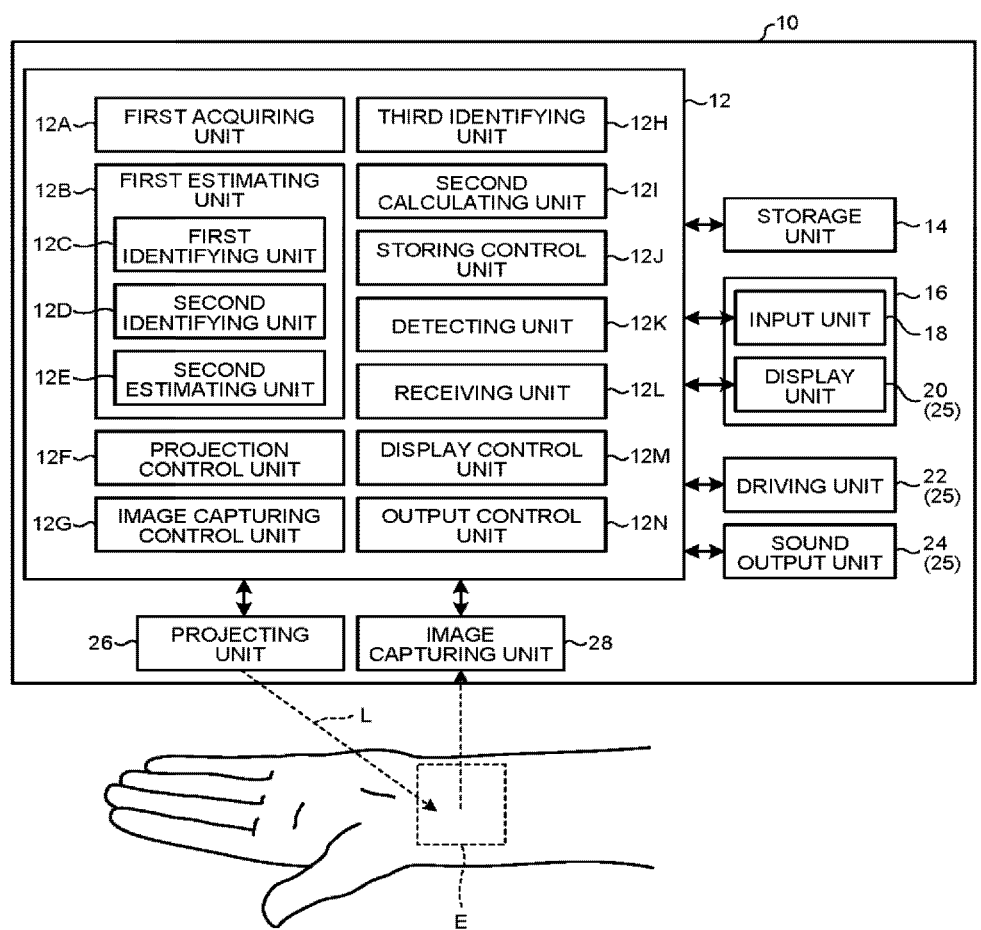
FIG. 1 is a block diagram illustrating a functional configuration of a biological component estimating apparatus.

FIG. 1 is an exemplary block diagram illustrating a functional configuration of a biological component estimating apparatus 10 according to the present embodiment.

The biological component estimating apparatus 10 is an apparatus for estimating the amount of change in a biological component in a biological body. Examples of the biological body include humans and animals other than the humans. The biological component represents a component included in the biological body. Specifically, the biological component is a component of a blood sample. Examples of the biological component include blood sugar (specifically, glucose) and water.

In the description below, as an example, the biological component estimating apparatus 10 is explained to estimate the amount of change in a blood glucose level, as an example of the amount of change in a biological component. However, the amount of change in a biological component estimated by the biological component estimating apparatus 10 may be any biological component, without limitation to the amount of change in the blood glucose level.

In the present embodiment, the biological component estimating apparatus 10 estimates the amount of change in the blood glucose level from a measurement target region E of the biological body. The measurement target region E is a certain region of the skin of the biological body.

The biological component estimating apparatus 10 includes a control unit 12, a storage unit 14, an input unit 18, a display unit 20, a driving unit 22, a sound output unit 24, a projecting unit 26, and an image capturing unit 28.

The storage unit 14, the input unit 18, the display unit 20, the driving unit 22, the sound output unit 24, the projecting unit 26, and the image capturing unit 28 are connected to the control unit 12 in such a manner that data and signals can be exchanged.

Explained in the present embodiment is an example in which the biological component estimating apparatus 10 is an integration of the control unit 12, the storage unit 14, the input unit 18, the display unit 20, the driving unit 22, the sound output unit 24, the projecting unit 26, and the image capturing unit 28. It is, however, also possible to allow at least one of the control unit 12, the storage unit 14, the input unit 18, the display unit 20, the driving unit 22, the sound output unit 24, the projecting unit 26, and the image capturing unit 28, included in the biological component estimating apparatus 10, to be provided separately from the other functional units.

The input unit 18 is a functional unit allowing a user to make various operation inputs. The input unit 18 is a combination of one or more of a mouse, a button, a remote controller, a keyboard, a voice recognition apparatus such as a microphone, and an image recognition apparatus.

The display unit 20 is a known display device for displaying various types of images. An example of the display unit 20 is a liquid crystal display (LCD).

The input unit 18 and the display unit 20 may be configured integrally. Specifically, the input unit 18 and the display unit 20 may be provided as a user interface (UI) unit 16 having both of an input function and a display function. An example of the UI unit 16 is an LCD with a touch panel.

The driving unit 22 is a driving unit that causes the biological component estimating apparatus 10 to vibrate. The driving unit 22 causes the biological component estimating apparatus 10 to vibrate under the control of the control unit 12. The sound output unit 24 is a functional unit for outputting sound. An example of the sound output unit 24 is a speaker.

At least one of the display unit 20, the driving unit 22, and the sound output unit 24 functions as an output unit 25 that outputs various types of information to the external of the biological component estimating apparatus 10. The biological component estimating apparatus 10 may also be configured not to include at least one of the driving unit 22 and the sound output unit 24.

The projecting unit 26 projects light onto the measurement target region E of the biological body. An example of the projecting unit 26 is a projector. The light projected to the measurement target region E includes a wavelength range in a near infrared range. The near infrared range is a range of wavelengths from 0.7 micrometers to 2.5 micrometers, for example.

In the present embodiment, the projecting unit 26 projects structured illumination L to the measurement target region E. The structured illumination L is light having a periodic structure of a given spatial frequency. The light making up the structured illumination L includes a wavelength range in the near infrared range, as mentioned earlier.

The projecting unit 26 projects the structured illumination L to the measurement target region E under the control of the control unit 12. The spatial frequency of the structured illumination L is adjusted under the control of the control unit 12.

The light of the structured illumination L projected onto the measurement target region E of the biological body enters the biological body, and is absorbed and scattered. A part of light scattered in the biological body is also scattered the external of the biological body.

The image capturing unit 28 captures a scattered reflection image resultant of such scattered light. Specifically, the image capturing unit 28 photographs the measurement target region E to which the structured illumination L is projected, and acquires a scattered reflection image resultant of the light of the structured illumination L projected to the measurement target region E.

The storage unit 14 stores therein various types of data. In the present embodiment, the storage unit 14 stores therein a reference template, an abnormal amount of change, first information, second information, and third information.

The reference template is a representation of a predetermined shape having a size smaller than a scattering coefficient distribution image (which will be described later in detail). The reference template has a rectangle shape, for example. Specifically, the reference template is a rectangular image that is smaller in size than the scattering coefficient distribution image. The reference template is, however, not limited to an image, and may also be data representing (e.g., coordinate data) such a shape having such a size.

The reference template having a predetermined size and shape is stored in the storage unit 14 in advance. The size and shape of the reference template may be modifiable by a user making operations on the input unit 18.

The scattering coefficient distribution image is a two-dimensional image having each pixel specified with the corresponding scattering coefficient of the measurement target region E of the biological body. The scattering coefficient is a scattering coefficient of the measurement target region E for the light including wavelengths in the near infrared range. The scattering coefficient distribution image is generated by the control unit 12 (in the manner to be described later in detail).

The abnormal amount of change represents an amount change in the blood glucose level rendered as abnormal from the medical point of view. The abnormal amount of change is stored in the storage unit 14 in advance. The abnormal amount of change may be modifiable by a user making operations on the input unit 18.

The first information is information in which an acquisition timing, the corresponding amount of change in the blood glucose level, and tracking information are associated with each other. The first information may also include another type of information in which additional information is associated with the information listed above.

The second information is information in which a first time period is associated with an abnormal amount of change. The third information is information in which an amount of change in the blood glucose level is associated with an amount of change in the scattering coefficient.

FIGS. 2A, 2B, and 2C are exemplary schematics of data structures of the first information 30, the second information 32, and the third information 34, respectively.

FIG. 2A is an exemplary schematic of a data structure of the first information 30. In the example illustrated in FIG. 2A, the first information 30 is information in which a user ID, a measurement ID, acquisition timing, an amount of change in the blood glucose level, and tracking information are associated with each other. The data format of the first information 30 is not limited to the format illustrated in FIG. 2A, and may be a table or a database, for example.

The user ID is identification information for identifying a user using the biological component estimating apparatus 10. The measurement ID is information for identifying a measurement timing. The measurement timing represents the timing of a measurement covering the duration of one cycle starting from when the biological component estimating apparatus 10 has received a power supply and starts estimating the amount of change in the blood glucose level to when the biological component estimating apparatus 10 ends the estimation of the amount of change in the blood glucose level based on the same measurement target region E in the biological body, or to when the power supply is shut off (that is, the biological component estimating apparatus 10 is powered off).

The acquisition timing represents the timing at which the control unit 12 acquires a scattering coefficient distribution image which will be described later. More specifically, the acquisition timing is the same as one of the timings at which a plurality of diffuse reflection images (which will be described later in detail) are captured, the diffuse reflection images being used in generating a scattering coefficient distribution image. For example, the acquisition timing matches the earliest one of the timings at which a plurality of respective diffuse reflection images used in generating a scattering coefficient distribution image are captured. The acquisition timing includes a year, a month, a date, hours, minutes, and seconds, for example.

In the example illustrated in FIG. 2A, the acquisition timing is at a cycle of 10 minutes. However, the acquisition timing is not limited to the cycle of 10 minutes, and may be any cycle between one minute or ten minutes, or any other timing.

An amount of change in the blood glucose level is calculated for each of the scattering coefficient distribution images (in other words, at every acquisition timing) and registered to the first information 30.

The amount of change in the blood glucose level represents an amount of change with respect to a reference blood glucose level. The reference blood glucose level represents an amount of change in the blood glucose level at one acquisition timing with respect to the blood glucose level at another acquisition timing set as a reference, for example. Specifically, the blood glucose level at the acquisition timing represents the blood glucose level of the measurement target region E of the biological body, at the timing at which the scattered reflection image used in generating the acquired scattering coefficient distribution image is captured.

The blood glucose level set as a reference is, for example, the blood glucose level at the first (initial) acquisition timing, among those belonging to the measurement timings identified with the same measurement ID and with the same user ID, for example. The blood glucose level set as a reference may also be the blood glucose level at the previous acquisition timing, for example.

The amount of change in the blood glucose level registered in the first information 30 is calculated by a process performed by the control unit 12 which will be described later, and registered in the first information 30 in a manner associated with the acquisition timing.

The tracking information is information used in correcting variations in the measurement target region E of the biological body. During the time in which the projecting unit 26 is projecting the structured illumination L to the same measurement target region E of the biological body, and the image capturing unit 28 is capturing the images of the measurement target region E, the area to which the structured illumination L is projected or the area captured by the image capturing unit 28 may be displaced depending on the acquisition timing, due to a movement of the biological body, for example. The tracking information is used in correcting the variation of the measurement target region E resultant of such a displacement.

The tracking information includes a reference template, a first pattern, and a relative position. The reference template is the same as that described above.

The first pattern is an image representing the path and the size of a biological body structure captured in the scattering coefficient distribution image. The first pattern is an image capturing a path of at least one of a blood vessel, a muscle, a tendon, and a ligament included in the biological body (the measurement target region E), for example.

The first pattern is identified in a scattering coefficient distribution image or an absorption coefficient distribution image (which will be described later in detail) by a process performed by the control unit 12 which will also be described later.

The relative position represents a relative position of the reference template with respect to the first pattern within the scattering coefficient distribution image. The relative position represents, for example, the position of the reference template with respect to the first pattern in the scattering coefficient distribution image, as a direction, a distance (number of pixels), or a rotational angle. The relative position may also be a relative position of the reference template with respect to the first pattern in the absorption coefficient distribution image having been acquired at the same timing as the scattering coefficient distribution image.

The relative position is calculated by a process performed by the control unit 12 which will be described later.

FIG. 2B is an exemplary schematic of a data structure of the second information 32. The second information 32 is information in which a first time period is associated with an abnormal amount of change corresponding to the first time period. The first time period represents a time period requiring some attention from the medical point of view with regard to the amount of change in the biological component, for example, depending on the type of the biological component that is used as the target of the measurement.

For example, when the biological component is blood glucose, the amount of change in the blood glucose level during an early morning time period may require some attention from the medical point of view. In such a case, the first time period is a time period representing early morning (e.g., 3 o'clock ante meridiem (AM) to 8 o'clock AM). The abnormal amount of change associated with the first time period represents the amount of change in the blood glucose level considered abnormal from the medical point of view during the first time period that is associated with the amount of change.

The second information 32 is stored in the storage unit 14 in advance. The number of pairs of the first time period and the abnormal amount of change stored in the second information 32 is not limited to one. In other words, the second information 32 may store therein a plurality of pairs of the first time period and the abnormal amount of change. The second information 32 may be modifiable by a user making instructions through operations.

FIG. 2C is an exemplary schematic of a data structure of the third information 34. The third information 34 is information in which the amount of change in the blood glucose level is associated with the amount of change in the scattering coefficient.

The scattering coefficient of the biological body for the light is correlated with a blood glucose concentration (in other words, a blood glucose level).

Figure 3:
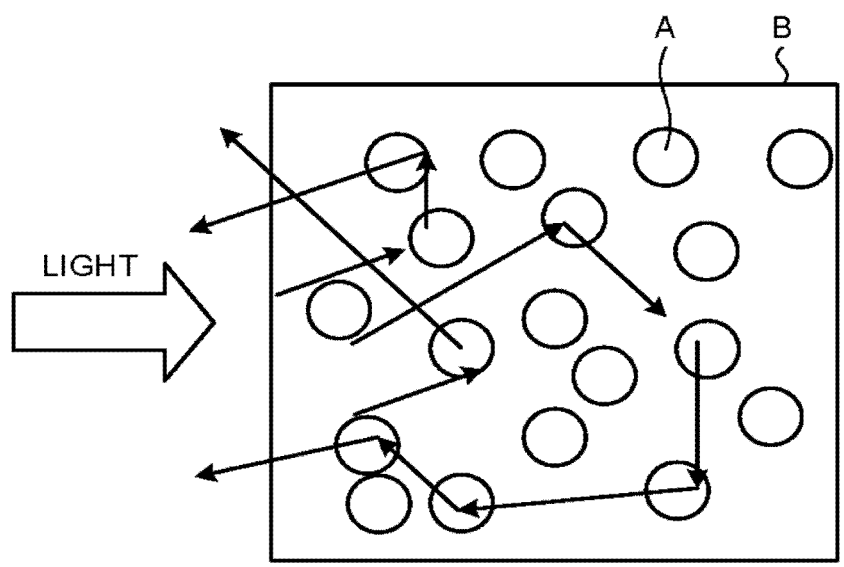
FIG. 3 is a schematic for explaining a scattering coefficient of a biological body for light.

FIG. 3 is a schematic for explaining how the light scatters in the biological body. The light scatters on the biological body due to the difference between the refractive index of extracellular fluid (ECF) B and that of fine floating particles A such as cell components and protein aggregate.

The refractive index nECF of the extracellular fluid B for the light in the near infrared range is from 1.35 to 1.36. The refractive index nS of fine floating particles A serving as scattering bodies is from 1.35 to 1.41. When the glucose concentration in the biological body increases, the refractive index of the extracellular fluid B also increases. Denoting this increase in the refractive index as δnglcose, the difference Δn between the refractive index of the extracellular fluid B and that of the fine floating particles A can be expressed as the following Equation (A).

$$\Delta n = nS - nECF + \delta nglcose \tag{A}$$

As indicated by Equation (A), the refractive index difference Δn decreases when the glucose concentration increases. The scattering coefficients in the biological body comply with the Mie scattering theoretical model. Therefore, when the refractive index difference Δn decreases, the scattering coefficient of the biological body also decreases.

For example, the scattering coefficient changes at a ratio of 0.6% mM-1 (0.33%/(10 mg/dL)) with respect to an amount of change in the blood glucose concentration.

The biological component estimating apparatus 10 according to the present embodiment measures or calculates an amount of change in the blood glucose level with respect to an amount of change in the scattering coefficient in advance. The biological component estimating apparatus 10 then registers the measured or calculated amount of change in the scattering coefficient in the third information 34, in a manner associated with the amount of change in the blood glucose level.

Referring back to FIG. 1, the control unit 12 controls the biological component estimating apparatus 10. The control unit 12 includes a first acquiring unit 12A, a first estimating unit 12B, a projection control unit 12F, an image capturing control unit 12G, a third identifying unit 12H, a second calculating unit 12I, a storing control unit 12J, a detecting unit 12K, a receiving unit 12L, a display control unit 12M, and an output control unit 12N.

Some or all of the first acquiring unit 12A, the first estimating unit 12B, the projection control unit 12F, the image capturing control unit 12G, the third identifying unit 12H, the second calculating unit 12I, the storing control unit 12J, the detecting unit 12K, the receiving unit 12L, the display control unit 12M, and the output control unit 12N may be implemented by causing a processor such as a central processing unit (CPU) to execute a computer program, that is, implemented as software, or may be implemented as hardware such as an integrated circuit (IC), or as a combination of software and hardware.

The projection control unit 12F controls the projecting unit 26. The image capturing control unit 12G controls the image capturing unit 28. The receiving unit 12L receives user operations on the input unit 18.

The first acquiring unit 12A acquires the scattering coefficient distribution image. The scattering coefficient distribution image is an image having each pixel specified with the corresponding scattering coefficient of the measurement target region E of the biological body, as described earlier.

The first acquiring unit 12A acquires a plurality of scattering coefficient distribution images for a measurement target region E positioned at the same position. In other words, the first acquiring unit 12A acquires a plurality of scattering coefficient distribution images at one measurement timing.

In the present embodiment, the first acquiring unit 12A also acquires the absorption coefficient distribution images. The first acquiring unit 12A acquires an absorption coefficient distribution image and a scattering coefficient distribution image as a pair at each acquisition timing.

The absorption coefficient distribution image is an image having each pixel specified with the corresponding absorption coefficient for light. The light includes a wavelength range in the near infrared range, as described earlier.

The first acquiring unit 12A may acquire a plurality of scattering coefficient distribution images and a plurality of absorption coefficient distribution images from the storage unit 14 or from an external apparatus.

In the example explained in the present embodiment, the first acquiring unit 12A generates a scattering coefficient distribution image and an absorption coefficient distribution image from the diffuse reflection images captured by the image capturing unit 28.

FIGS. 4A to 4F are schematics for explaining the generation of a scattering coefficient distribution image and an absorption coefficient distribution image.

To begin with, the first acquiring unit 12A controls the projecting unit 26 to project the structured illumination L at a plurality of different spatial frequencies $f_k$ (where k is an integer equal to or greater than one, and equal to or smaller than "a", where "a" is an integer equal to or greater than two) to the measurement target region E.

At this time, the first acquiring unit 12A controls the projecting unit 26 to project the structured illumination L at different phases ($2\pi p/m$ (where "m" is an integer equal to or greater than three, and "p" is an integer satisfying |p|≤m)) to the measurement target region E for each of the different spatial frequencies $f_k$. The first acquiring unit 12A controls the projecting unit 26 to output the structured illumination L at each of the spatial frequencies $f_k$, while shifting the phase equally in an increment of $2\pi p/m$.

Specifically, the first acquiring unit 12A transmits a projection instruction including a spatial frequency $f_k$ and a phase $2\pi p/m$ to the projecting unit 26. The projecting unit 26 receiving the projection instruction projects the structured illumination L at the spatial frequency $f_k$ and at the phase $2\pi p/m$ included in the projection instruction onto the measurement target region E. For example, the projecting unit 26 generates the structured illumination L by modulating a sine wave with the spatial frequency $f_k$ and the phase $2\pi p/m$ included in the projection instruction, and projects the structured illumination L to the measurement target region E.

The image capturing unit 28 then captures an image of the measurement target region E every time the projecting unit 26 projects the structured illumination L to the measurement target region E, and acquires the scattered reflection image. The image capturing unit 28, as a result, acquires a scattered reflection image corresponding to each of the spatial frequencies $f_k$ and the phases $2\pi p/m$ included in the projection instruction.

Figure 4A:
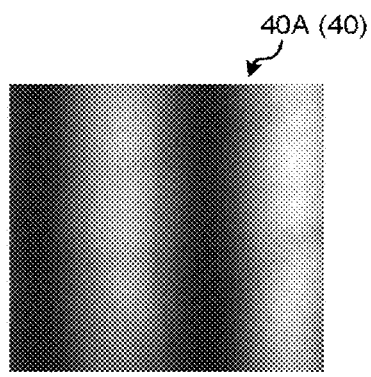
FIGS. 4A to 4F are schematics for explaining generation of a scattering coefficient distribution image and an absorption coefficient distribution image.
Figure 4B:
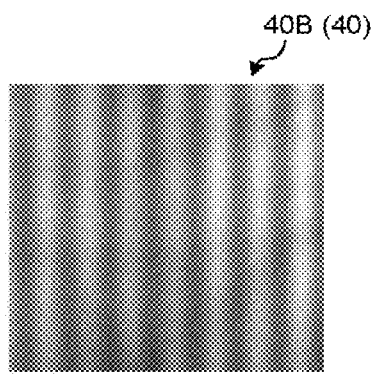

FIGS. 4A and 4B are exemplary schematics of the scattered reflection image 40. FIG. 4A is an exemplary schematic of a scattered reflection image 40A when the structured illumination L at the spatial frequency f1 is projected. FIG. 4B is an exemplary schematic of a scattered reflection image 40B when the structured illumination L at the spatial frequency f2 is projected.

In the example illustrated in FIGS. 4A and 4B, the light at wavelengths of 660 nanometers±5 nanometers is used as the light of the structured illumination L. However, the light of the structured illumination L may be any light including wavelengths in the near infrared range, and is not limited to the light in the wavelength range mentioned above. Because an absorption coefficient and a scattering coefficient of a biological body for light exhibit wavelength-dependent characteristics, it is preferable to keep the wavelength range within ±10 nanometers for the light of the structured illumination L.

The image capturing unit 28 acquires "m" diffuse reflection images 40 at the respective different phases $2\pi p/m$, for each of the different spatial frequencies $f_k$. In other words, the image capturing unit 28 acquires a plurality of diffuse reflection images 40 at the respective different phases for one spatial frequency $f_k$.

The first acquiring unit 12A calculates, at each of the spatial frequencies $f_k$, a diffuse amplitude ($M_{ac}(r, f_k)$) for each pixel, using the diffuse reflection images 40 captured by the image capturing unit 28 with the projecting light at the respective different phases at the spatial frequency $f_k$. "r" in $M_{ac}(r, f_k)$ represents the position of the specific pixel. In other words, the first acquiring unit 12A generates a diffuse amplitude image having each pixel specified with a diffuse amplitude, from the diffuse reflection images 40.

Figure 4C:
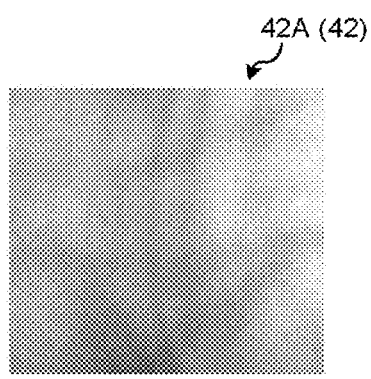
Figure 4D:
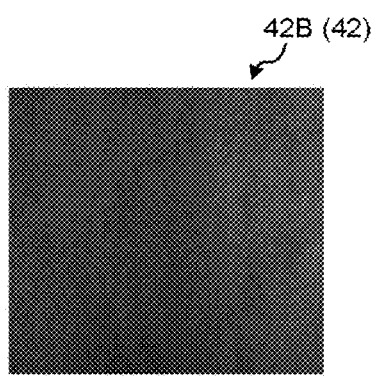

FIGS. 4C and 4D are exemplary schematics of a diffuse amplitude image 42. FIG. 4C is an exemplary schematic of a diffuse amplitude image 42A calculated using a plurality of diffuse reflection images including the scattered reflection image 40A illustrated in FIG. 4A captured by projecting the light at a plurality of respective different phases. FIG. 4D is an exemplary schematic of a diffuse amplitude image 42B calculated using a plurality of diffuse reflection images including the scattered reflection image 40B illustrated in FIG. 4B captured by projecting the light at the respective different phases.

The first acquiring unit 12A prepares a calibration sample with a known absorption coefficient and scattering coefficient. The calibration sample is a model phantom of the biological body with a known absorption coefficient and scattering coefficient, for example. The model phantom of the biological body preferably has a uniform absorption coefficient and scattering coefficient. The calibration sample is prepared in advance. The first acquiring unit 12A then acquires a plurality of diffuse reflection images 40 at the respective different phases, at each of the spatial frequencies $f_k$ (hereinafter, referred to as calibration diffuse reflection images), in the same manner as that explained above.

The first acquiring unit 12A then calculates, at each of the spatial frequencies $f_k$, a diffuse amplitude ($M_{ac,\,ref}(r, f_k)$) for each pixel, using the calibration diffuse reflection images. "r" in $M_{ac,\,ref}(r, f_k)$ represents the position of the specific pixel. In other words, the first acquiring unit 12A generates a calibration diffuse amplitude image having each pixel specified with a diffuse amplitude, from the calibration diffuse reflection images.

A diffuse reflectance of the biological body for the light of the structured illumination L can be expressed as Equation (1) analytically. Equation (1) below is an equation representing the diffuse reflectance obtained by applying a spatial sine-wave modulated light source to a diffusion equation resultant of diffusion-approximation of the radiative transfer equation (RTE).

$$R_d(f_k) = \frac{3Aa'}{(\mu'_{eff}/\mu_{tr}+1)(\mu'_{eff}/\mu_{tr}+3A)} \quad (1)$$

$R_d(f)$ in Equation (1) represents the diffuse reflectance. $f_k$ represents the spatial frequency. "A" represents a proportionality coefficient, which is expressed as Equation (2) below.

$$A = \frac{1-R_{eff}}{2(1+R_{eff})}; \quad (2)$$

-continued
$$R_{eff} \approx 0.0636 n + 0.668 + \frac{0.710}{n} - \frac{1.440}{n^2}$$

"n" in Equation (2) represents the refractive index of the "n" biological body at the wavelength used in the measurement.

$\mu_{tr}$ in Equation (1) represents a transfer coefficient, which is expressed by Equation (3). $\mu_{eff}$ and $\mu'_{eff}$ in Equation (1) are expressed as Equation (4) and Equation (5), respectively. "a'" is an reduced albedo, which is expressed as Equation (6).

$$\mu_{tr}=(\mu_a+\mu_s') \quad (3)$$

$\mu_a$ in Equation (3) represents an absorption coefficient, and $\mu'_s$ represents an reduced scattering coefficient.

$$\mu_{eff} = (3\mu_a\mu_{tr})^{1/2} \quad (4)$$

$$\mu'_{eff} = (\mu_{eff}^2 + (2\pi f_k)^2)^{1/2} \quad (5)$$

$$a' = \frac{\mu'_s}{\mu_{tr}} \quad (6)$$

The first acquiring unit 12A substitutes the parameters in Equation (1) with the absorption coefficient and the scattering coefficient of the calibration sample. In this manner, the first acquiring unit 12A acquires the diffuse reflectance $R_d(f_k)$ of the calibration sample for the light of the structured illumination L at each of the spatial frequencies $f_k$. Hereinafter, the diffuse reflectance $R_d(f_k)$ of the calibration sample for each pixel at each of the spatial frequencies $f_k$ will be denoted as $R_{d,\,ref}(r, f_k)$.

The first acquiring unit 12A then acquires the diffuse reflectance $R_d(r, f_k)$ for each pixel, in the measurement target region E of the biological body at each of the spatial frequencies $f_k$, using Equation (7) below.

$$R_d(r, f_k) = \frac{M_{ac}(r, f_k)}{M_{ac,ref}(r, f_k)} \cdot R_{d,ref}(r, f_k) \quad (7)$$

The first acquiring unit 12A then calculates an absorption coefficient $\mu_a$ and an reduced scattering coefficient $\mu'_s$ for each pixel from the diffuse reflectance $R_d(r, f_k)$ for each pixel, at each of the spatial frequencies $f_k$.

In the present embodiment, the first acquiring unit 12A uses non-linear regression to calculate the absorption coefficient $\mu_a$ and the reduced scattering coefficient $\mu'_s$ for each pixel.

Figure 5:
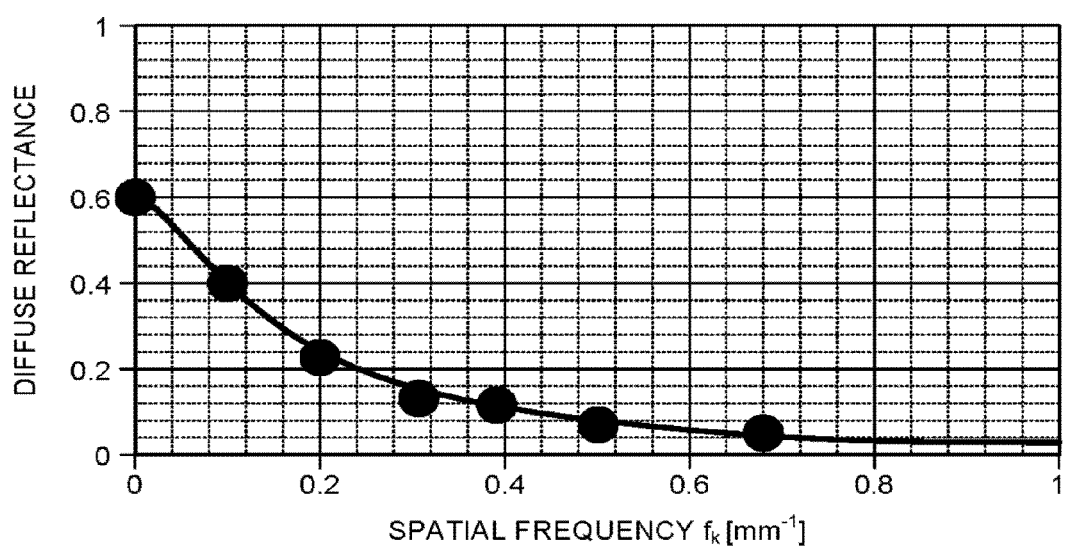
FIG. 5 is a chart illustrating a relation between a spatial frequency and a diffuse reflectance.

FIG. 5 is a chart illustrating a relation between a spatial frequency $f_k$ and a diffuse reflectance in a particular pixel. The first acquiring unit 12A plots the calculated diffuse reflectance $R_d(r, f_k)$ to the corresponding spatial frequency $f_k$ for each pixel.

These measurement points (plot) follow Equation (1), which is the diffusion equation. The first acquiring unit 12A therefore calculates the absorption coefficient $\mu_a$ and the reduced scattering coefficient $\mu'_s$ through non-linear regression with the function expressed as Equation (1).

The first acquiring unit 12A then generates a scattering coefficient distribution image having each pixel specified with the corresponding scattering coefficient of the measurement target region E of the biological body, by plotting the reduced scattering coefficient $\mu'_s$ calculated for each pixel, to the corresponding pixel position.

The first acquiring unit 12A also generates an absorption coefficient distribution image having each pixel specified with the corresponding absorption coefficient of the measurement target region E of the biological body, by plotting the absorption coefficient $\mu_a$ calculated for each pixel, to the corresponding pixel position.

Figure 4E:
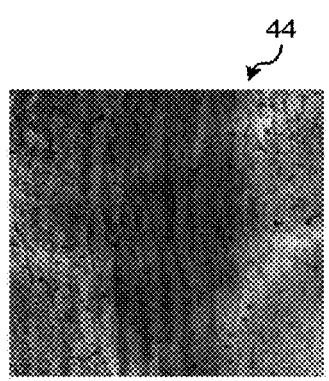
Figure 4F:
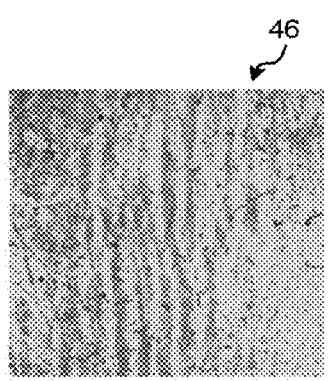

FIG. 4E is a schematic of an example of an absorption coefficient distribution image 44. FIG. 4F is a schematic of an example of a scattering coefficient distribution image 46.

Hemoglobin in the biological body absorbs a large portion of the light at a wavelength of 660 nanometers. Therefore, the path of a vein near the skin surface in the measurement target region E of the biological body is clearly visualized in the absorption coefficient distribution image 44, as illustrated in FIG. 4E.

In the manner described above, the first acquiring unit 12A acquires a scattering coefficient distribution image 46 and an absorption coefficient distribution image 44 of the measurement target region E. In other words, in the present embodiment, the first acquiring unit 12A acquires a scattering coefficient distribution image 46 and an absorption coefficient distribution image 44 by generating the scattering coefficient distribution image 46 and the absorption coefficient distribution image 44 from the diffuse reflection images 40.

The first acquiring unit 12A acquires at least the scattering coefficient distribution image 46. However, it is preferable for the first acquiring unit 12A to acquire both of the scattering coefficient distribution image 46 and the absorption coefficient distribution image 44.

At each measurement timing, the first acquiring unit 12A repeats this sequence of projecting the structured illumination L at the changed spatial frequency and phase onto the measurement target region E and acquiring the absorption coefficient distribution image 44 and the scattering coefficient distribution image 46 from the diffuse reflection images 40 by capturing images of the measurement target region E. By repeating this sequence, the first acquiring unit 12A acquires a plurality of absorption coefficient distribution images 44 and a plurality of scattering coefficient distribution images 46.

Specifically, an "acquisition timing" mentioned above is representation of a unit of the sequences in which the structured illumination L at the changed spatial frequency and phase is projected to the measurement target region E, a plurality of diffuse reflection images 40 are acquired at each of the respective spatial frequencies and phases by capturing images of the measurement target region E, and a pair of the absorption coefficient distribution image 44 and the scattering coefficient distribution image 46 is acquired from the diffuse reflection images 40.

The first acquiring unit 12A acquires a plurality of pairs of the absorption coefficient distribution image 44 and the scattering coefficient distribution image 46 at different acquisition timings, each of which is a representation of this sequence.

Referring back to FIG. 1, the first estimating unit 12B estimates the amount of change in the biological component based on the scattering coefficient distribution image 46 acquired by the first acquiring unit 12A. In the present embodiment, the first estimating unit 12B estimates the amount of change in the blood glucose level.

The first estimating unit 12B calculates a scattering coefficient for each of the scattering coefficient distribution images 46 having different acquisition timings but the same measurement ID (measurement timing). The first estimating unit 12B calculates a scattering coefficient representative of each of the scattering coefficient distribution images 46 by calculating the arithmetic average of the scattering coefficients specified in the pixels for each of the scattering coefficient distribution images 46.

The first estimating unit 12B then calculates, for each of the scattering coefficient distribution images 46 acquired at the respective acquisition timings and having the same measurement ID (measurement timing), the amount of change in the scattering coefficient, with respect to the scattering coefficient in another scattering coefficient distribution image 46 serving as a reference. The other scattering coefficient distribution image 46 serving as a reference is the scattering coefficient distribution image 46 acquired at the previous acquisition timing, as described earlier, for example. The first estimating unit 12B then reads the amount of change in the blood glucose level that is associated with the calculated amount of change in the scattering coefficient, from the third information 34 (see FIG. 2C). In this manner, the first estimating unit 12B estimates the amount of change in the blood glucose level at each acquisition timing.

The first estimating unit 12B may define the scattering coefficient serving as a reference in advance. The first estimating unit 12B may then calculate, for each of the scattering coefficient distribution images 46 acquired at the respective acquisition timings, the difference in the scattering coefficient with respect to the reference scattering coefficient, as an amount of change in the scattering coefficient at the corresponding acquisition timing. The first estimating unit 12B may then read the amount of change in the blood glucose level associated with the calculated amount of change in the scattering coefficient from the third information 34 (see FIG. 2C). In this manner, too, the first estimating unit 12B can estimate the amount of change in the blood glucose level at each acquisition timing.

In the manner described above, the biological component estimating apparatus 10 according to the present embodiment estimates the amount of change in the biological component based on the scattering coefficient distribution images 46. Therefore, the amount of change in the biological component can be estimated accurately using scattering coefficient distribution images non-invasively, without requiring repeated drawing of blood by needling.

It is also possible to draw blood by needling and to measure the blood glucose level using an enzyme through the known method in at least one of a plurality of acquisition timings. In such a case, the first estimating unit 12B stores the blood glucose level at the acquisition timing in the storage unit 14. The first estimating unit 12B then calculates the amount by which the scattering coefficient represented by another scattering coefficient distribution image 46 has changed with respect to that represented by the scattering coefficient distribution image 46 at the corresponding acquisition timing for which the blood glucose level is determined. The first estimating unit 12B then calculates the sum of the calculated amount of change and the blood glucose level at the acquisition timing for which the blood glucose level has been determined, as the blood glucose level at the acquisition timing for which the amount of change is calculated. In this manner, the first estimating unit 12B can estimate the varying blood glucose level less invasively and accurately.

During the time in which the projecting unit 26 is projecting the structured illumination L to the same measurement target region E, and during the time in which the image capturing unit 28 is capturing images of the measurement target region E, the area to which the structured illumination L is projected or the area captured by the image capturing unit 28 may be displaced, due to a movement of the biological body, for example.

Therefore, it is preferable for the first estimating unit 12B to estimate the amount of change in the blood glucose level (biological component) based on a first area, which is a partial area of the scattering coefficient distribution image 46.

In such a case, it is preferable for the first estimating unit 12B to include a first identifying unit 12C, a second identifying unit 12D, and a second estimating unit 12E.

The first identifying unit 12C identifies a first pattern included in the scattering coefficient distribution image 46. The first pattern is an image representing the path and the size of the biological body structure included in the scattering coefficient distribution image 46, as described earlier.

The first identifying unit 12C reads the first pattern associated with the current measurement ID from the first information 30 (see FIG. 2A). The tracking information including the first pattern registered in the first information 30 is generated using the absorption coefficient distribution image 44 and the scattering coefficient distribution image 46 acquired at the first one of the acquisition timings corresponding to that measurement ID (the process of which will be described later in detail).

The first identifying unit 12C identifies the first pattern included in the scattering coefficient distribution image 46. In other words, the first identifying unit 12C identifies an area representing the path of the biological body structure matching the read first pattern in the scattering coefficient distribution image 46. Any known pattern matching may be used to identify the first pattern in the scattering coefficient distribution image 46.

Figure 6A:
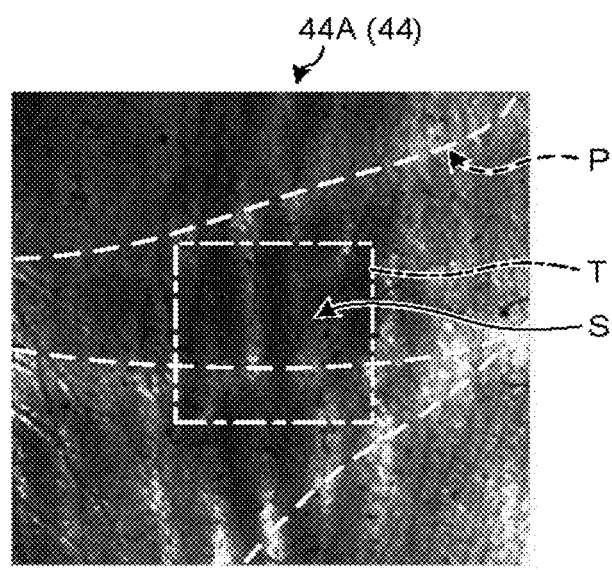
FIGS. 6A and 6B are schematics illustrating an exemplary absorption coefficient distribution image and scattering coefficient distribution image, respectively.
Figure 6B:
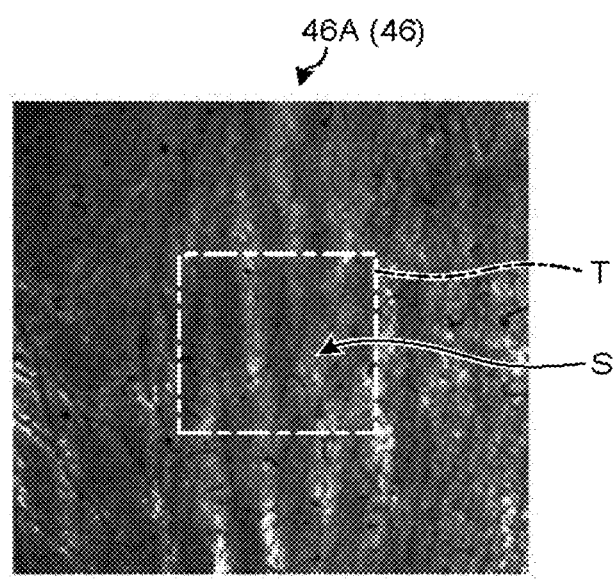

FIGS. 6A and 6B are schematics illustrating examples of the absorption coefficient distribution image 44 and the scattering coefficient distribution image 46, respectively. FIGS. 6A and 6B are schematics illustrating the absorption coefficient distribution image 44A and the scattering coefficient distribution image 46A, respectively, acquired at the same acquisition timing.

For example, the first identifying unit 12C identifies an area representing the path of the biological body structure that matches the first pattern P in the scattering coefficient distribution image 46A.

The pattern of a blood vessel such as that of a vein can be identified more easily in the absorption coefficient distribution image 44 than in the scattering coefficient distribution image 46. By contrast, a muscle, a tendon, or a ligament pattern can be identified more easily in the scattering coefficient distribution image 46 than in the absorption coefficient distribution image 44.

In this manner, the pattern of a biological body structure is sometimes more identifiable in the absorption coefficient distribution image 44A (see FIG. 6A) than in the scattering coefficient distribution image 46A (see FIG. 6B), depending on the measurement target region E.

In such a case, to begin with, the first identifying unit 12C identifies an area representing the path of the biological body structure that matches the first pattern P from the absorption coefficient distribution image 44A. The first identifying unit 12C then places the identified first pattern P onto the scattering coefficient distribution image 46A acquired at the same acquisition timing as the absorption coefficient distribution image 44A.

More specifically, the first identifying unit 12C reads the pixel positions of the respective pixels constituting the identified first pattern P from the absorption coefficient distribution image 44A. The first identifying unit 12C then identifies the pattern represented by the pixels at the read pixel positions in the scattering coefficient distribution image 46A acquired at the same acquisition timing, as the first pattern P. In this manner, the first identifying unit 12C identifies the first pattern P included in the scattering coefficient distribution image 46A.

As described above, the pattern of a blood vessel such as that of a vein can be identified more easily in the absorption coefficient distribution image 44 than in the scattering coefficient distribution image 46. In the absorption coefficient distribution image 44, the pattern of a blood vessel is represented as an area brighter than the other area. Therefore, the first identifying unit 12C may also use the absorption coefficient distribution image 44A itself (the entire absorption coefficient distribution image 44A) as the first pattern P. In other words, the first identifying unit 12C may use the absorption coefficient distribution image 44A itself (the entire absorption coefficient distribution image 44A) as a template used for the pattern matching.

The second identifying unit 12D identifies the area inside of a reference template T that is positioned at the relative position with respect to the identified first pattern P in the scattering coefficient distribution image 46, as a first area S.

The second identifying unit 12D reads the relative position included in the tracking information that is associated with the current measurement ID from the first information 30 (see FIG. 2A). The second identifying unit 12D then places the reference template T at the read relative position with respect to the identified first pattern P, in the scattering coefficient distribution image 46.

For example, as illustrated in FIG. 6B, the second identifying unit 12D places the reference template T in the scattering coefficient distribution image 46A. The position where the reference template T is placed in the scattering coefficient distribution image 46A is the same as the read relative position with respect to the first pattern P in the absorption coefficient distribution image 44A (see FIG. 6A) acquired at the same acquisition timing.

The second identifying unit 12D then identifies the area inside of the reference template T placed in the scattering coefficient distribution image 46A as the first area S.

The second estimating unit 12E then estimates the amount of change in the biological component (for example, the blood glucose level) based on the scattering coefficients specified in the respective pixels constituting the identified first area S in the scattering coefficient distribution image 46A.

More specifically, the second estimating unit 12E calculates an arithmetic average of the scattering coefficients specified in the respective pixels constituting the identified first area S, as a scattering coefficient corresponding to the scattering coefficient distribution image 46A.

The second estimating unit 12E then calculates the amount by which the current scattering coefficient having been just calculated has changed with respect to the scattering coefficient corresponding to the previous acquisition timing that is associated with the same measurement ID (measurement timing).

The second estimating unit 12E then reads the amount of change in the blood glucose level associated with the calculated amount of change in the scattering coefficient from the third information 34 (see FIG. 2C). In this manner, the second estimating unit 12E estimates the amount of change in the blood glucose level.

In the manner described above, the first estimating unit 12B can correct the variation of the measurement target region E of the biological body, by estimating the amount of change in the blood glucose level (biological components) based on the first area S, which is a partial area of the scattering coefficient distribution image 46.

Figure 7A:
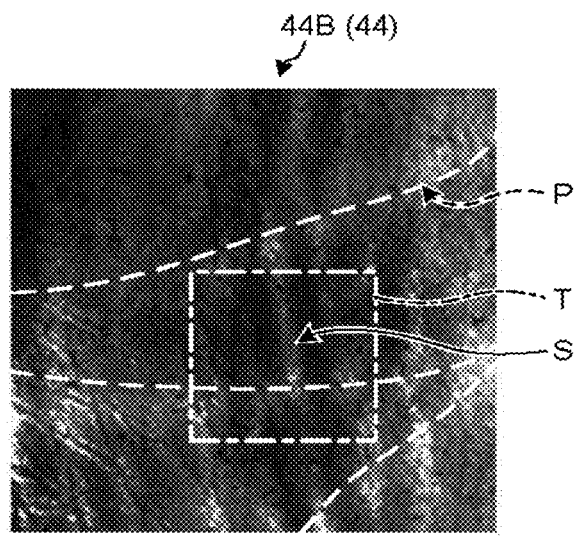
FIGS. 7A and 7B are schematics illustrating an example of a displacement of a measurement target region.
Figure 7B:
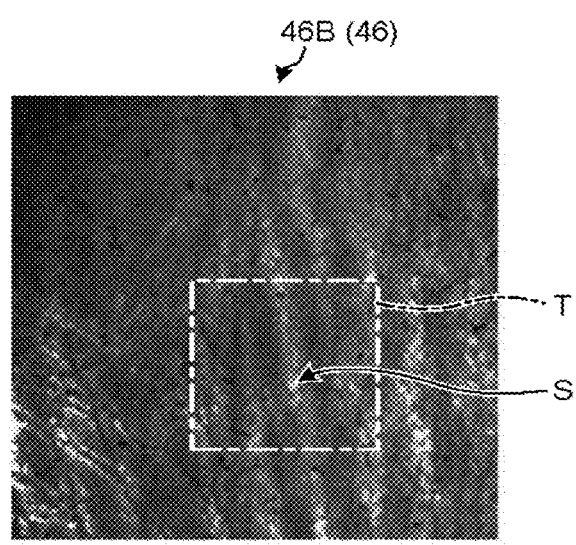

FIGS. 7A and 7B are schematics illustrating examples of an absorption coefficient distribution image 44B and a scattering coefficient distribution image 46B, with the measurement target region E slightly displaced with respect to the position at the acquisition timing at which the scattering coefficient distribution image 46A and the absorption coefficient distribution image 44A illustrated in FIGS. 6A and 6B, respectively, are acquired.

As illustrated in FIG. 7A, the first pattern P in the absorption coefficient distribution image 44B is displaced with respect to that in the absorption coefficient distribution image 44A (see FIG. 6A).

As illustrated in FIG. 7A, even when the position or the angle of the first pattern P in the absorption coefficient distribution image 44B is displaced, the relative position of the reference template T with respect to the first pattern P remains the same. The first pattern represents the path of a blood vessel, a muscle, a tendon, a ligament, or the like, and such a path does not change very much within several hours to several tens of hours during which the transition in the amount of change in the blood glucose level is being monitored. Furthermore, because the first pattern represents the path of a biological body structure (such as a blood vessel), the path does not change very much even when the thickness of the blood vessel changes due to a change in the posture or the blood pressure of the subject, for example. The path represented by the first pattern delineates a unique pattern depending on the subject or the measurement target region E.

Therefore, the first estimating unit 12B can estimate the amount of change in the blood glucose level using the first area S inside of the constant reference template T, the relative position of which with respect to the first pattern P always remains the same, in the scattering coefficient distribution image 46.

In other words, the first area S inside the reference template T placed in the scattering coefficient distribution image 46B (see FIG. 7B) acquired at the same acquisition timing as the absorption coefficient distribution image 44B represents the same area of the biological body as the first area S inside the reference template T placed in the scattering coefficient distribution image 46A (see FIG. 6B) acquired at a different acquisition timing.

Therefore, even when the area to which the structured illumination L is projected is displaced or when the area captured by the image capturing unit 28 is displaced due to a movement of the biological body, for example, it is possible to suppress the reduction in the estimation accuracy of the amount of change in the biological component, due to such a displacement.

In other words, by allowing the first estimating unit 12B to estimate the amount of change in the blood glucose level based on the first area S, which is a partial area of the scattering coefficient distribution image 46, the amount of change in the biological component can be estimated more accurately.

The tracking information such as the first pattern corresponding to each of the measurement IDs (measurement timings) is generated by the third identifying unit 12H, the second calculating unit 12I, and the storing control unit 12J, and registered in the first information 30.

Specifically, the third identifying unit 12H performs image analysis on the scattering coefficient distribution image 46 or the absorption coefficient distribution image 44 acquired at the first acquisition timing, among a plurality of scattering coefficient distribution images 46 associated with the same measurement ID (measurement timing), and identifies the pattern of the biological body structure included in the scattering coefficient distribution image 46 as the first pattern. The pattern is an image in which the path of the biological body structure is captured.

For example, a plurality of types of reference patterns, each representing a basic path that can be identified as a biological body structure, such as a blood vessel, a muscle, a tendon, or a ligament, are stored in the storage unit 14 in advance.

The third identifying unit 12H then performs the pattern matching, for example, using known image processing, to identify the part representing the same path at least partially as the basic pattern in the scattering coefficient distribution image 46 acquired at the first acquisition timing, as the first pattern.

When a plurality of scattering coefficient distribution images 46 that are associated with the same measurement ID have already been acquired, the third identifying unit 12H identifies the pattern of the biological body structure in one of the scattering coefficient distribution images 46 associated with the same measurement ID as the first pattern. In other words, the scattering coefficient distribution image 46 in which the first pattern is identified is not limited to the scattering coefficient distribution image 46 acquired at the first acquisition timing.

As mentioned earlier, the pattern of a blood vessel such as that of a vein can be identified more easily in the absorption coefficient distribution image 44 than in the scattering coefficient distribution image 46. By contrast, the pattern of a muscle, a tendon, or a ligament can be identified more easily in the scattering coefficient distribution image 46 than in the absorption coefficient distribution image 44.

Therefore, it is preferable for the third identifying unit 12H to identify the first pattern, using both of the absorption coefficient distribution image 44 and the scattering coefficient distribution image 46 acquired at the first acquisition timing.

This difference will now be explained with reference to FIGS. 6A and 6B. It is assumed therein that the absorption coefficient distribution image 44A and the scattering coefficient distribution image 46A respectively illustrated in FIGS. 6A and 6B are the absorption coefficient distribution image 44 and the scattering coefficient distribution image 46 acquired at the first acquisition timing.

In the example illustrated in FIGS. 6A and 6B, the absorption coefficient distribution image 44A (see FIG. 6A) allows the pattern of the biological body structure to be identified more easily than the scattering coefficient distribution image 46A (see FIG. 6B). In such a case, the third identifying unit 12H identifies the pattern of the biological body structure included in the absorption coefficient distribution image 44A as the first pattern P (see FIG. 6A).

There are some other cases in which the scattering coefficient distribution image 46A allows the pattern of the biological body structure to be identified more easily than the absorption coefficient distribution image 44A. In such a case, the third identifying unit 12H identifies the pattern of the biological body structure in the scattering coefficient distribution image 46A as the first pattern P.

The second calculating unit 12I places the reference template in the absorption coefficient distribution image 44A from which the first pattern P is identified. The second calculating unit 12I then calculates the relative position of the placed reference template with respect to the identified first pattern P, in the absorption coefficient distribution image 44A (see FIG. 6A).

When the third identifying unit 12H identifies the first pattern P from the scattering coefficient distribution image 46A, the second calculating unit 12I places the reference template T in the scattering coefficient distribution image 46A. The second calculating unit 12I then calculates the relative position of the placed reference template with respect to the identified first pattern P, in the scattering coefficient distribution image 46A (see FIG. 6B).

As mentioned earlier, the reference template T represents a predetermined shape (for example, a rectangular frame) with a size smaller than that of the scattering coefficient distribution image 46A (the scattering coefficient distribution image 46). The scattering coefficient distribution image 46 has the same size as the absorption coefficient distribution image 44. Therefore, the size of the reference template T is also smaller than the absorption coefficient distribution image 44A (the absorption coefficient distribution image 44).

The reference template T may be placed at any position in the scattering coefficient distribution image 44A or the scattering coefficient distribution image 46A, as long as the entire frame represented by the reference template T fits inside of the scattering coefficient distribution image 46A or the absorption coefficient distribution image 44B. Furthermore, it is preferable for the reference template T to be placed in such a manner that at least a part of the reference template T is not continuous to (not brought into contact with) an end of the scattering coefficient distribution image 46A or the absorption coefficient distribution image 44A. This is because the ends of the scattering coefficient distribution image 46A and the absorption coefficient distribution image 44A may fail to be captured at the next acquisition timing, due to displacement of the measurement target region E.

The storing control unit 12J then stores the first pattern P identified by the third identifying unit 12H, the relative position calculated by the second calculating unit 12I, and the reference template T, in the storage unit 14 in a manner associated with the current measurement ID. More specifically, the storing control unit 12J creates the tracking information by associating the first pattern P identified by the third identifying unit 12H, the relative position, and the reference template T, with one another, and registers the tracking information to the first information 30 in a manner associated with the measurement ID associated with the acquisition timing at which absorption coefficient distribution image 44A or the scattering coefficient distribution image 46A in which the first pattern P is identified is acquired.

As a result, the tracking information (the reference template, the first pattern, and the relative position) is registered to the first information 30 in a manner associated with the corresponding measurement ID, as illustrated in FIG. 2A. The same reference template T may be, however, shared among different measurement IDs. The reference template T may be therefore not registered to the first information 30, and may be stored separately in the storage unit 14.

Referring back to FIG. 1, the display control unit 12M displays various images on the display unit 20.

For example, the display control unit 12M displays an image representing the amount of change in the biological component (for example, blood glucose level) estimated by the first estimating unit 12B on the display unit 20.

Examples of the image representing the amount of change in the biological component include a graph or a chart presenting temporal transitions of the amount of change, and an image presenting numbers representing the amount of change.

At this time, it is preferable for the display control unit 12M to display a section representing an abnormal amount of change in the image representing the amount of change in the biological component (for example, blood glucose level) estimated by the first estimating unit 12B, on the display unit 20 in a display mode that is different from a display mode in which the other section is displayed. A different display mode is a mode presenting at least one of the color, the brightness, a blinking interval, and a size (e.g., thickness) differently.

Figure 8:
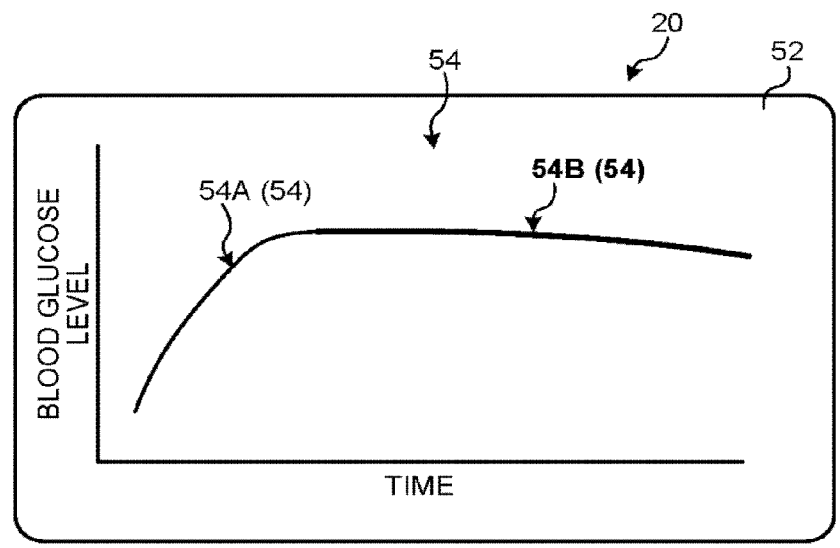
FIG. 8 is a schematic illustrating an exemplary display screen.

FIG. 8 is an exemplary schematic of a display screen 52 presenting an image representing the amount of changes in the blood glucose level. The display control unit 12M displays the display screen 52 on the display unit 20, for example.

In the example illustrated in FIG. 8, the display screen 52 includes a chart 54 indicating the amount of change in the blood glucose level against time, as the image representing the amount of change in the blood glucose level. For example, a part of the chart 54 is the normal section 54A, and the other part is an abnormal section 54B. The normal section 54A is a section of the acquisition timing (time) during which the amount of change in the blood glucose level is normal. The abnormal section 54B is a section of the acquisition timing (time) during which the amount of change in the blood glucose level is abnormal. It is preferable for the display control unit 12M to display the abnormal section 54B in a display mode that is different from a display mode in which the normal section 54A is displayed.

Specifically, the display control unit 12M reads the abnormal amount of change from the storage unit 14. The display control unit 12M then identifies a section indicating the abnormal amount of change, from the amount of change in the blood glucose level at each acquisition timing and estimated by the first estimating unit 12B. The display control unit 12M then displays the identified section indicating the abnormal amount of change (abnormal section 54B) in a display mode that is different from a display mode in which the other section (normal section 54A) is displayed on the display unit 20.

Referring back to FIG. 1, the detecting unit 12K detects a positional displacement of the image capturing unit 28 with respect to the measurement target region E. The detecting unit 12K detects the positional displacement when the first identifying unit 12C is incapable of identifying the first pattern P in the absorption coefficient distribution image 44 and the scattering coefficient distribution image 46.

In other words, there are some cases in which the path of the corresponding first pattern P cannot be identified in the absorption coefficient distribution image 44 and the scattering coefficient distribution image 46 that are acquired at a particular acquisition timing. In such a case, if the amount of change in the blood glucose level is measured using the same area, the estimation accuracy of the amount of change in the blood glucose level may deteriorate.

To address this issue, the detecting unit 12K detects the positional displacement when the corresponding first pattern P cannot be recognized in the absorption coefficient distribution image 44 and the scattering coefficient distribution image 46 that are acquired at the particular acquisition timing.

When the detecting unit 12K has detected a positional displacement, it is preferable for the display control unit 12M to display the information indicating the positional displacement on the display unit 20. The information representing the positional displacement may include a message recommending correction of the position of the measurement target region E of the biological body.

Figure 9:
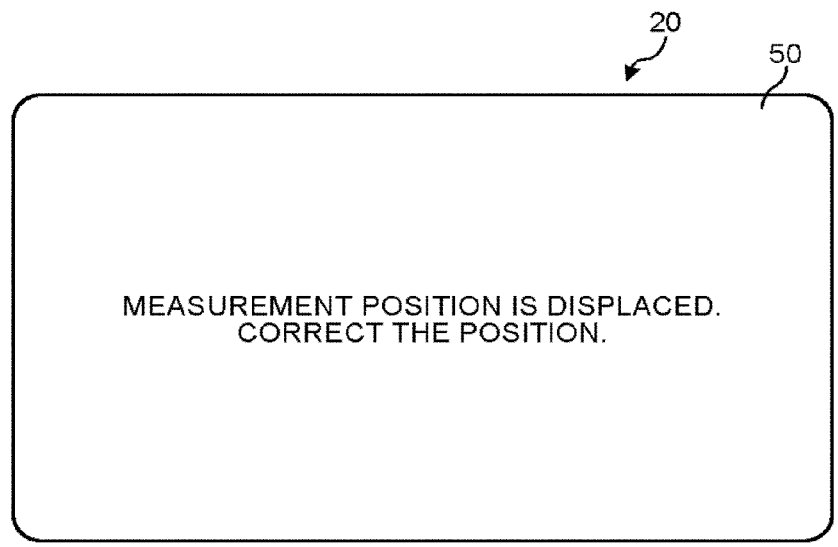
FIG. 9 is a schematic illustrating another exemplary display screen.

FIG. 9 is an exemplary schematic of a display screen 50 for the information indicating a positional displacement. When the detecting unit 12K has detected a positional displacement, the display control unit 12M displays the information representing the positional displacement or a message recommending correction of the position such as "Measurement position is displaced. Correct the position." on the display unit 20.

Therefore, the biological component estimating apparatus 10 according to the present embodiment can easily provide a user with the information indicating that the measurement target region E is displaced.

Referring back to FIG. 1, the output control unit 12N controls the output unit 25. As mentioned earlier, the display unit 20, the driving unit 22, and the sound output unit 24 function as the output unit 25 for outputting various types of information to the external of the biological component estimating apparatus 10.

The output control unit 12N controls the output unit 25 to output information indicating abnormality when the amount of change in the biological component (for example, blood glucose level) estimated based on the scattering coefficient distribution image 46 that is generated from the diffuse reflection images 40 captured during a predetermined first time period represents a predetermined abnormal amount of change.

The output control unit 12N reads the first time period from the second information 32 (see FIG. 2B) stored in the control unit 12. The output control unit 12N then determines whether the timing at which the diffuse reflection images 40, from which the amount of change estimated by the first estimating unit 12B is calculated, are captured is within the first time period. If the timing is within the first time period, the output control unit 12N determines whether the amount of change in the blood glucose level estimated based on the diffuse reflection images 40 captured at such a timing matches the abnormal amount of change corresponding to the first time period specified in the second information 32. If the output control unit 12N determines that the amount of change matches the abnormal amount of change, the output control unit 12N then controls the output unit 25 to output information representing the abnormality.

Specifically, the output control unit 12N controls at least one of the display unit 20, the driving unit 22, and the sound output unit 24 to output information representing the abnormality.

More specifically, the output control unit 12N controls the output unit 25 to output information indicating the abnormality by controlling the driving unit 22 to cause the biological component estimating apparatus 10 to vibrate. As another example, the output control unit 12N controls the output unit 25 to output information indicating the abnormality by controlling the sound output unit 24 to output a predetermined sound. As yet another example, the output control unit 12N controls the output unit 25 to output information indicating the abnormality by displaying a predetermined message representing the abnormality to the display unit 20.

Through such a process performed by the output control unit 12N, when an amount of change in the blood glucose level considered to be abnormal from the medical point of view is estimated during the first time period requiring some attention from the medical point of view, the subject can be presented with information indicating that the estimation result of the amount of change in the blood glucose level represents abnormality.

A biological component estimating process performed by the biological component estimating apparatus 10 according to the present embodiment will now be explained.

Figure 10:
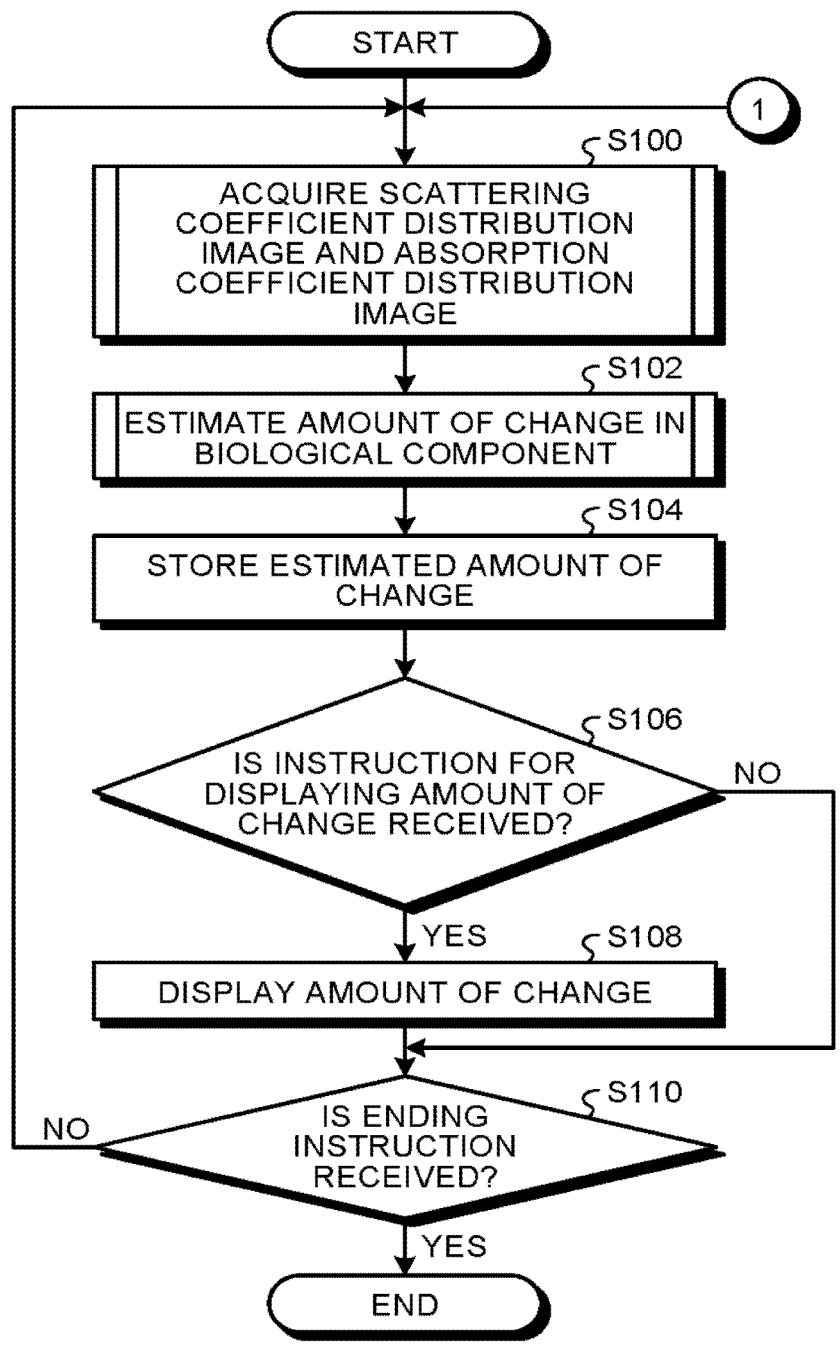
FIG. 10 is a flowchart illustrating a biological component estimating process.

FIG. 10 is a flowchart illustrating the biological component estimating process performed by the biological component estimating apparatus 10 according to the present embodiment. The control unit 12 in the biological component estimating apparatus 10 performs the process illustrated in FIG. 10 at each measurement timing (measurement ID) associated with one user identified by the corresponding user ID. Every time the process is completed for each measurement ID (measurement timing), the biological component estimating apparatus 10 increments the measurement ID.

To begin with, the first acquiring unit 12A acquires the scattering coefficient distribution image 46 and the absorption coefficient distribution image 44 (Step S100).

The first estimating unit 12B then estimates the amount of change in the biological component based on the scattering coefficient distribution image 46 and the absorption coefficient distribution image 44 acquired at Step S100 (Step S102).

The first estimating unit 12B then stores the estimated amount of change in the biological component in the control unit 12 in a manner associated with the current measurement ID and acquisition timing (Step S104).

The receiving unit 12L then determines whether an instruction for displaying the amount of change in the biological component has been received (Step S106). If the input unit 18 has received an input of the instruction for displaying the amount of change in the biological component from a user, for example, the input unit 18 outputs the instruction to the control unit 12. The receiving unit 12L in the control unit 12 makes this determination at Step S106 by determining whether an input of the instruction for displaying the amount of change in the biological component is received from the input unit 18.

If the receiving unit 12L determines to be Yes at Step S106 (Yes at Step S106), the process is shifted to Step S108. At Step S108, the display control unit 12M displays the image representing the amount of change in the biological component on the display unit 20 (Step S108). The process is then shifted to Step S110.

If the receiving unit 12L determines to be No at Step S106 (No at Step S106), the process is shifted to Step S110.

At Step S110, the receiving unit 12L determines whether an ending instruction has been received from the input unit 18 (Step S110). Users can give an instruction for ending the measurement by making an operation on the input unit 18. When an instruction for ending the measurement is provided by a user through the operation on the input unit 18, the input unit 18 outputs the instruction for ending the measurement to the control unit 12. The receiving unit 12L in the control unit 12 determines whether the instruction for ending the measurement has been received from the input unit 18.

If the receiving unit 12L determines to be No at Step S110 (No at Step S110), the process is returned to Step S100.

If the receiving unit 12L determines to be Yes at Step S110 (Yes at Step S110), this routine is ended.

Figure 11:
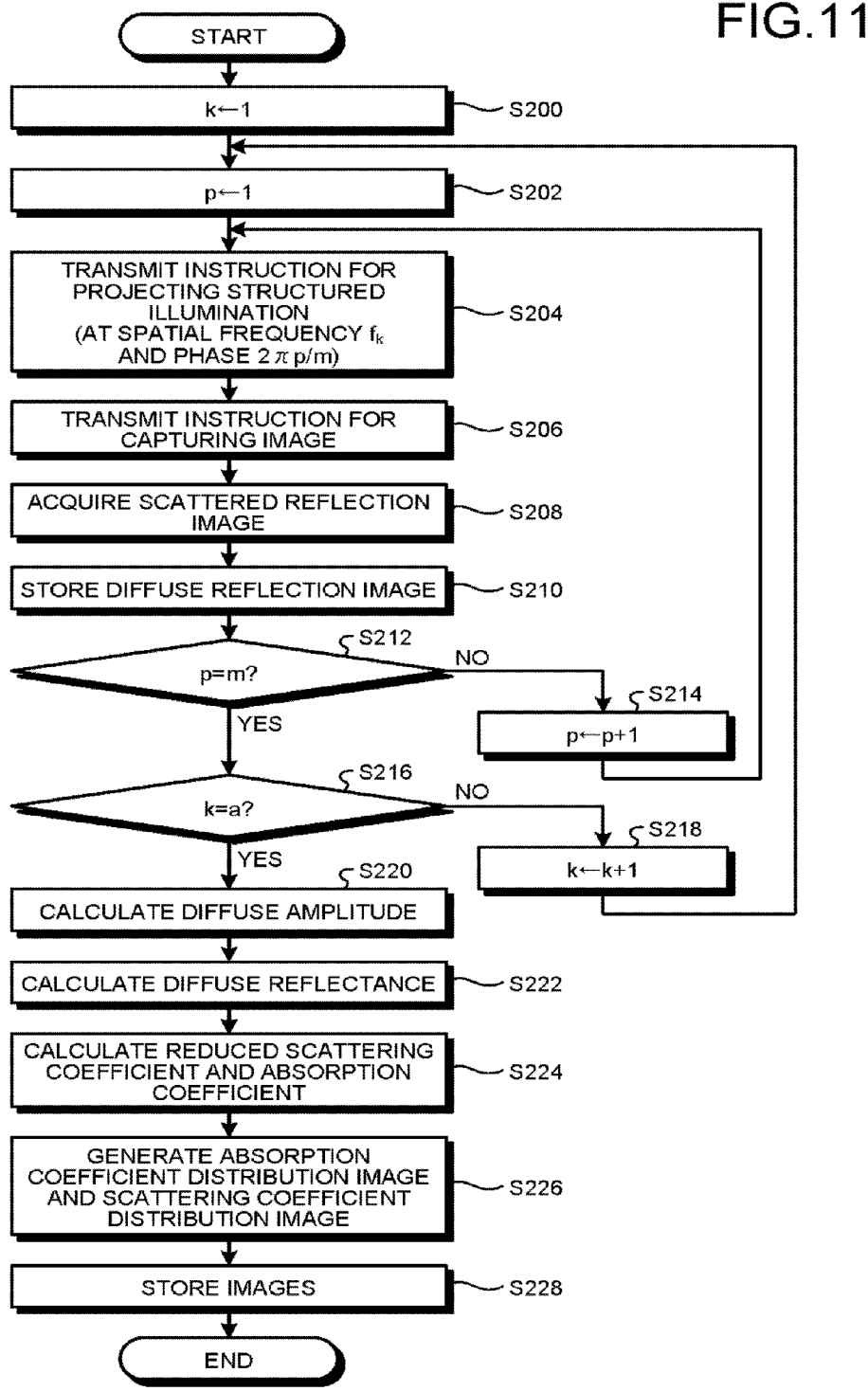
FIG. 11 is a flowchart illustrating the process at Step S100 in FIG. 10.

The process at Step S100 will now be explained in detail. FIG. 11 is a flowchart illustrating the process at Step S100 in FIG. 10.

To begin with, the first acquiring unit 12A sets "k" representing the spatial frequency $f_k$ to one (Step S200). The first acquiring unit 12A then sets "p" representing the phase ($2\pi p/m$) to one (Step S202).

The first acquiring unit 12A then transmits a projection instruction containing the set spatial frequency $f_k$ and phase $2\pi p/m$ to the projecting unit 26 (Step S204). The projecting unit 26 that has received the projection instruction projects the structured illumination L at the spatial frequency $f_k$ and the phase $2\pi p/m$ included in the projection instruction to the measurement target region E.

The image capturing control unit 12G transmits an instruction for capturing an image of the measurement target region E to the image capturing unit 28 (Step S206). The image capturing unit 28 then acquires a scattered reflection image 40 by capturing an image of the measurement target region E, and outputs the scattered reflection image 40 to the control unit 12. The first acquiring unit 12A acquires the scattered reflection image 40 from the image capturing unit 28 (Step S208). The first acquiring unit 12A then stores the acquired scattered reflection image 40 in the storage unit 14 (Step S210).

The first acquiring unit 12A then determines whether "p" in the phase ($2\pi p/m$) matches "m" that is the maximum value of "p" (Step S212). If the first acquiring unit 12A determines to be No at Step S212 (No at Step S212), the first acquiring unit 12A adds one to "p" (Step S214), and the process is returned to Step S204.

If the first acquiring unit 12A determines to be Yes at Step S212 (Yes at Step S212), the process is shifted to Step S216.

At Step S216, the first acquiring unit 12A determines whether "k" of the spatial frequency $f_k$ matches "a" that is the maximum value of "k" (Step S216). If the first acquiring unit 12A determines to be No at Step S216 (No at Step S216), the process is shifted to Step S218. At Step S218, the first acquiring unit 12A adds one to "k" (Step S218), and the process is returned to Step S202.

If the first acquiring unit 12A determines to be Yes at Step S216 (Yes at Step S216), the process is shifted to Step S220. At Step S220, the first acquiring unit 12A calculates the diffuse amplitude ($M_{ac}(r, f_k)$) for each pixel, at each of the spatial frequencies $f_k$, using a plurality of diffuse reflection images 40 captured at different phases at each of the spatial frequencies $f_k$ and acquired through the process at Steps S200 to S216 (Step S220).

The first acquiring unit 12A also performs the process from Steps S200 to S220 on the calibration sample as mentioned earlier, and calculates the diffuse amplitude ($M_{ac, ref}(r, f_k)$) for each pixel.

The first acquiring unit 12A then calculates the diffuse reflectance $R_d(r, f_k)$ for each pixel, in the measurement target region E of the biological body, at each of the spatial frequencies $f_k$, using Equation (7) (Step S222).

The first acquiring unit 12A then calculates the absorption coefficient $\mu_a$ and the reduced scattering coefficient $\mu'_s$ for each pixel from the diffuse reflectance $R_d(r, f_k)$ for each pixel, acquired at each of the spatial frequencies $f_k$ (Step S224).

The first acquiring unit 12A then generates the absorption coefficient distribution image 44 and the scattering coefficient distribution image 46 (Step S226). At Step S226, the first acquiring unit 12A generates the scattering coefficient distribution image 46 having each pixel specified with the corresponding scattering coefficient of the measurement target region E of the biological body, by placing the reduced scattering coefficient $\mu'_s$ calculated and estimated for each pixel at Step S224 to the corresponding pixel position.

The first acquiring unit 12A also generates the absorption coefficient distribution image 44 having each pixel specified with the corresponding absorption coefficient of the measurement target region E of the biological body, by placing the absorption coefficient $\mu_a$ calculated for each pixel at Step S224 to the corresponding pixel position.

Through the process at Step S224, the first acquiring unit 12A acquires the absorption coefficient distribution image 44 and the scattering coefficient distribution image 46.

The first acquiring unit 12A then stores the current measurement ID, and the generated absorption coefficient distribution image 44 and scattering coefficient distribution image 46 in the storage unit 14 in a manner associated with the acquisition timing at which the absorption coefficient distribution image 44 and the scattering coefficient distribution image 46 are acquired (Step S228). This routine is then ended.

Figure 12:
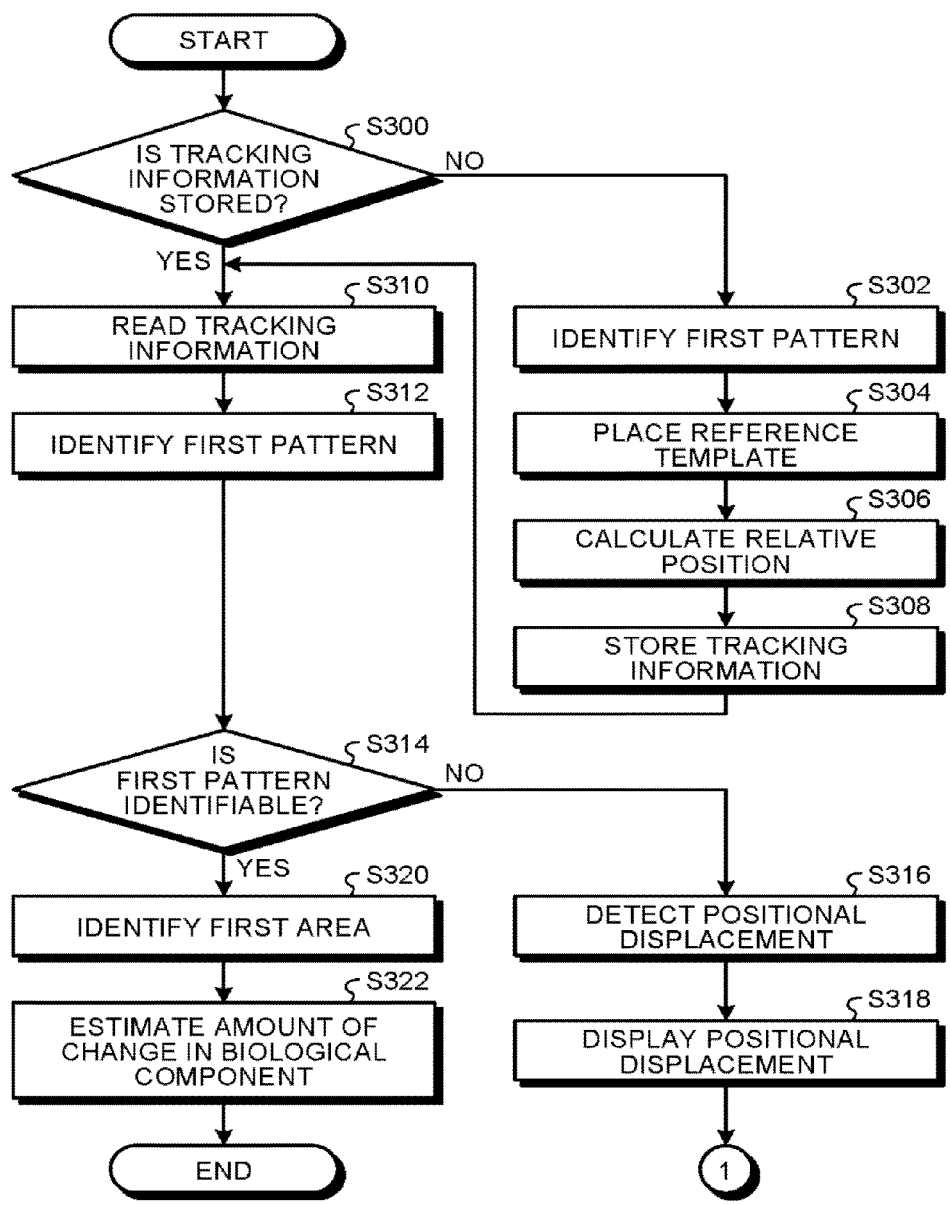
FIG. 12 is a flowchart illustrating the process at Step S102 in FIG. 10.

The process at Step S102 in FIG. 10 will now be explained in detail. FIG. 12 is a flowchart illustrating the process at Step S102 in FIG. 10.

To begin with, the first estimating unit 12B determines whether the tracking information has been stored in the storage unit 14 (Step S300). Specifically, the first estimating unit 12B makes the determination at Step S300 by determining whether the tracking information corresponding to the current measurement ID is stored in the first information 30 (see FIG. 2A). If the first estimating unit 12B determines to be Yes at Step S300 (Yes at Step S300), the process is shifted to Step S310 which will be described later.

If the first estimating unit 12B determines to be No at Step S300 (Step S300), the process is shifted to Step S302. At Step S302, the third identifying unit 12H identifies the pattern of the biological body structure included in the scattering coefficient distribution image 46 acquired at first acquisition timing, among those associated with the current measurement ID (measurement timing), as the first pattern (Step S302). The third identifying unit 12H may also identify the first pattern from the absorption coefficient distribution image 44, as mentioned earlier.

The second calculating unit 12I then places the reference template T in the scattering coefficient distribution image 46 from which the first pattern is identified at Step S302 (Step S304). The second calculating unit 12I then calculates the relative position of the placed reference template T with respect to the identified first pattern P in the scattering coefficient distribution image 46 in which the first pattern is identified at Step S302 (Step S306).

The storing control unit 12J then creates the tracking information by associating the first pattern P identified by the third identifying unit 12H at Step S302 with the relative position calculated by the second calculating unit 12I at Step S306 and the reference template T, and stores the tracking information in the storage unit 14 (Step S308). In other words, the storing control unit 12J registers the tracking information in the first information 30 (see FIG. 2A) in a manner associated with the current measurement ID. The process is then shifted to Step S310.

At Step S310, the first identifying unit 12C reads the tracking information corresponding to the current measurement ID from the first information 30 (Step S310).

The first identifying unit 12C then reads the absorption coefficient distribution image 44 and the scattering coefficient distribution image 46 acquired through the process at Step S100 (Steps S200 to S228 in FIGS. 10 and 11). The absorption coefficient distribution image 44 and the scattering coefficient distribution image 46 are the images acquired by the first acquiring unit 12A at the same acquisition timing. The first identifying unit 12C then identifies the first pattern included in the tracking information read at Step S310, in the absorption coefficient distribution image 44 or the scattering coefficient distribution image 46 (Step S312).

In other words, the first identifying unit 12C identifies an area representing the path of the biological body structure matching the first pattern in the scattering coefficient distribution image 46 or the absorption coefficient distribution image 44.

The detecting unit 12K then determines whether the first identifying unit 12C has been capable of identifying the first pattern P from the absorption coefficient distribution image 44 and the scattering coefficient distribution image 46 (Step S314). If the first identifying unit 12C has not been capable of identifying the first pattern P (No at Step S314), the detecting unit 12K detects a positional displacement (Step S316).

The display control unit 12M then displays the information representing the positional displacement on the display unit 20 (Step S318). The process is then returned to Step S100 (see FIG. 10). If the detecting unit 12K determines to be Yes at Step S314 (Yes at Step S314), the process is shifted to Step S320.

At Step S320, the second identifying unit 12D identifies the area inside of the reference template T placed at the relative position with respect to the first pattern P identified at Step S312 in the absorption coefficient distribution image 44 and the scattering coefficient distribution image 46, as the first area S (Step S320). The relative position used at Step S320 is the relative position included in the tracking information read at Step S310.

The second estimating unit 12E then estimates the amount of change in the blood glucose level based on the scattering coefficients specified in the respective pixels constituting the first area S identified at Step S320 in the scattering coefficient distribution image 46 (Step S322). The second estimating unit 12E then registers the estimated amount of change in the blood glucose level to the first information 30, in a manner associated with the current measurement ID and to the acquisition timing of the scattering coefficient distribution image 46 used in the estimation, and this routine is ended.

Figure 13:
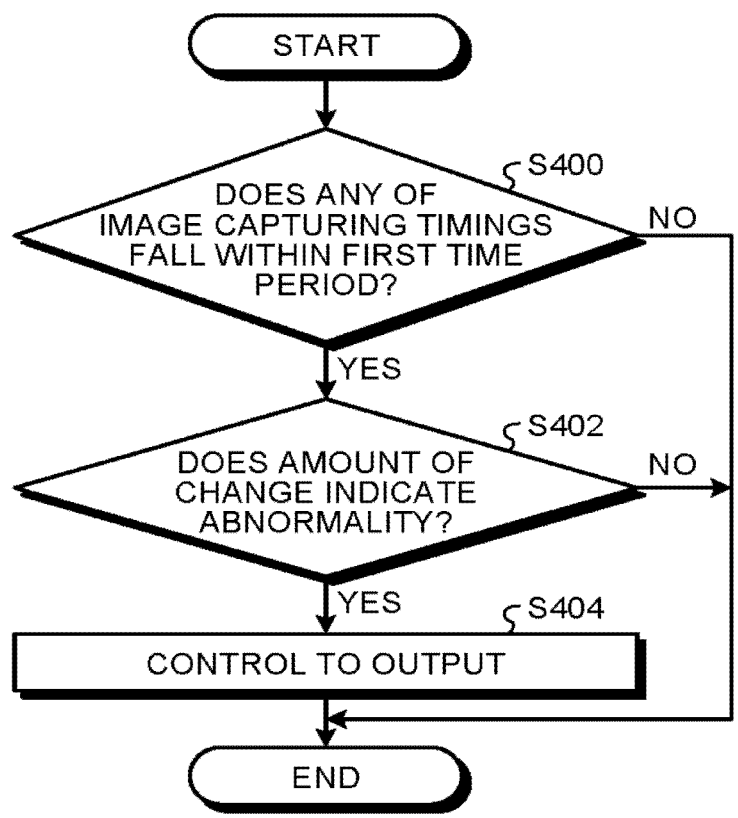
FIG. 13 is a flowchart illustrating an interruption process.

The biological component estimating apparatus 10 then performs an interrupting process. FIG. 13 is a flowchart illustrating the interrupting process performed by the biological component estimating apparatus 10.

The control unit 12 repeats the interrupting process illustrated in FIG. 13. To begin with, the output control unit 12N determines whether there is any image capturing timing falling within the first time period stored in the storage unit 14 (Step S400). For example, the output control unit 12N makes the determination at Step S400 by determining whether there is any image capturing timing falling within the first time period, among a plurality of image capturing timings associated with the current measurement ID and stored in the storage unit 14.

Every time the image capturing unit 28 acquires a scattered reflection image 40 by capturing an image of the measurement target region E, the image capturing control unit 12G stores the timing at which the scattered reflection image 40 is captured and the scattered reflection image 40 in the storage unit 14 in a manner associated with each other.

If the output control unit 12N determines to be No at Step S400 (No at Step S400), this routine is ended. If the output control unit 12N determines to be Yes at Step S400 (Yes at Step S400), the process is shifted to Step S402.

At Step S402, the output control unit 12N determines whether the amount of change in the blood glucose level estimated based on the scattering coefficient distribution image 46 that is generated from the diffuse reflection images 40 captured at the image capturing timing within the first time period matches the abnormal amount of change associated with the first time period in the second information 32 (see FIG. 2B) (Step S402). If the output control unit 12N determines to be No at Step S402 (No at Step S402), this routine is ended.

If the output control unit 12N determines to be Yes at Step S402 (Yes at Step S402), the process is shifted to Step S404. The output control unit 12N then controls the output unit 25 to output information representing abnormality at Step S404 (Step S404), and this routine is ended.

As explained above, the biological component estimating apparatus 10 according to the present embodiment includes the first acquiring unit 12A and the first estimating unit 12B. The first acquiring unit 12A acquires the scattering coefficient distribution image 46 having each pixel specified with the corresponding scattering coefficient of the measurement target region E of the biological body for the light including a wavelength range in the near infrared range. The first estimating unit 12B estimates the amount of change in the biological component based on the scattering coefficient distribution images 46.

In the manner described above, the biological component estimating apparatus 10 according to the present embodiment estimates the amount of change in a biological component based on a plurality of scattering coefficient distribution images. Therefore, with the biological component estimating apparatus 10 according to the present embodiment, it is no longer necessary to draw blood repeatedly from the subject by needling. Furthermore, because the scattering coefficient distribution image is used, the biological component estimating apparatus 10 can estimate an amount of change in the biological component highly accurately.

The biological component estimating apparatus 10 according to the present embodiment can therefore estimate an amount of change in the biological component non-invasively and accurately.

The biological component estimating apparatus 10 according to the present embodiment also includes the first acquiring unit 12A, the first estimating unit 12B, and the display control unit 12M. The first acquiring unit 12A acquires a scattering coefficient distribution image 46 having each pixel specified with the corresponding scattering coefficient of the measurement target region E of the biological body for the light including a wavelength range in the near infrared range. The first estimating unit 12B estimates the amount of change in the biological component based on the scattering coefficient distribution images 46. The display control unit 12M displays the image representing the estimated amount of change in the biological component on the display unit 20.

Therefore, the biological component estimating apparatus 10 according to the present embodiment can provide a user with the amount of change in the biological component easily, in addition to the advantageous effects described above.

Explained above for the biological component estimating apparatus 10 according to the present embodiment is an example in which the first estimating unit 12B estimates the amount of change in the blood glucose level (biological component) by performing pattern matching with the first pattern P included in the scattering coefficient distribution image 46, using the tracking information.

However, the biological component estimating apparatus 10 may be provided with a known detecting mechanism for detecting at least one of a movement of the biological body, an area to which the structured illumination L is projected, and an area captured by the image capturing unit 28. In such a case, the first estimating unit 12B corrects the displacement of the first area S in the scattering coefficient distribution image 46 by using the detection result of the detecting mechanism, and then estimates the amount of change in the blood glucose level (biological component).

Figure 14:
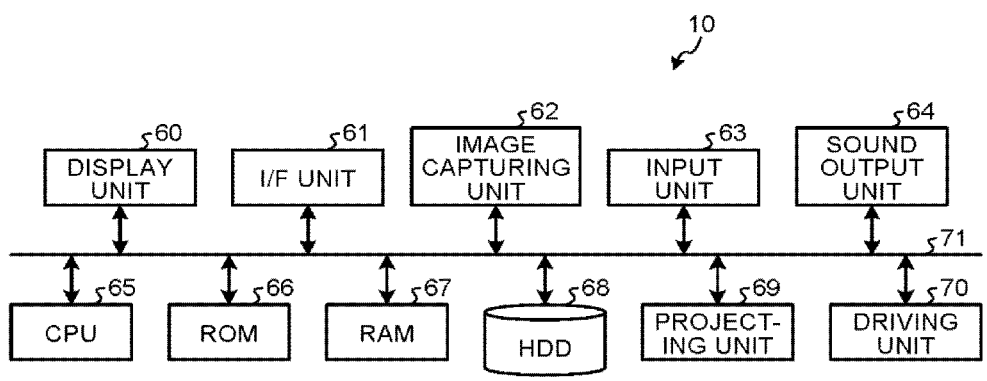
FIG. 14 is a block diagram illustrating an exemplary hardware configuration.

A hardware configuration of the biological component estimating apparatus 10 according to the present embodiment will now be explained. FIG. 14 is a block diagram illustrating an exemplary hardware configuration of the biological component estimating apparatus 10 according to the present embodiment.

The biological component estimating apparatus 10 according to the present embodiment includes a display unit 60, an interface (I/F) unit 61, an image capturing unit 62, an input unit 63, a sound output unit 64, a central processing unit (CPU) 65, a read-only memory (ROM) 66, a random access memory (RAM) 67, a hard disk drive (HDD) 68, a projecting unit 69, and a driving unit 70 that are connected to each other over a bus 71, and has a hardware configuration using a general computer.

The CPU 65 is a processor controlling the process of the entire biological component estimating apparatus 10. The RAM 67 stores therein data required for various processes performed by the CPU 65. The ROM 66 stores therein computer programs and the like for implementing the various processes performed by the CPU 65. The HDD 68 corresponds to the storage unit 14 described above. The I/F unit 61 is an interface for connecting to an external apparatus or to an external terminal over a communication circuit, and exchanging data with the external apparatus or the external terminal with which the connection is established. The display unit 60, the image capturing unit 62, the input unit 63, the sound output unit 64, the projecting unit 69, and the driving unit 70 correspond to the display unit 20, the image capturing unit 28, the input unit 18, the sound output unit 24, the projecting unit 26, and the driving unit 22, respectively.

The computer programs for executing the various processes executed in the biological component estimating apparatus 10 according to the present embodiment are incorporated and provided in the ROM 66 or the like in advance.

The computer programs executed in the biological component estimating apparatus 10 according to the present embodiment may also be recorded and provided in a computer-readable recording medium such as a compact disc read-only memory (CD-ROM), a flexible disk (FD), a compact disc recordable (CD-R), and a digital versatile disc (DVD), as a file in an installable or executable format in the apparatus.

Furthermore, the computer programs executed in the biological component estimating apparatus 10 according to the present embodiment may be stored in a computer connected to a network such as the Internet, and made available for download over the network. The computer programs for executing the processes in the biological component estimating apparatus 10 according to the present embodiment may also be provided or distributed over a network such as the Internet.

The computer programs for executing the various processes executed in the biological component estimating apparatus 10 according to the present embodiment can generate the units described above on the main memory.

The various types of information stored in the HDD 68, that is, the various types of information stored in the storage unit 14 may also be stored in an external apparatus (such as a server). In such a case, the external apparatus is connected to the CPU 65 over a network or the like.

While a certain embodiment has been described, the embodiment has been presented by way of example only, and is not intended to limit the scope of the inventions. Indeed, the novel embodiment described herein may be embodied in a variety of other forms; furthermore, various omissions, substitutions and changes in the form of the embodiment described herein may be made without departing from the spirit of the inventions. The accompanying claims and their equivalents are intended to cover such forms or modifications as would fall within the scope and spirit of the inventions.

What is claimed is:

1. A biological component estimating apparatus comprising:
   a processor configured to
      acquire a scattering coefficient distribution image having each pixel specified with a scattering coefficient of a measurement target region of a biological body for light including a wavelength range in a near infrared range,
      estimate an amount of change in a biological component based on the scattering coefficient distribution image, and
      store in a storage unit a reference template having a size smaller than a size of the scattering coefficient distribution image and also having a predetermined shape, a first pattern of a biological body structure included in the scattering coefficient distribution image, and a relative position of the reference template with respect to the first pattern in the scattering coefficient distribution image, wherein
   the processor is further configured to
      estimate the amount of change in the biological component based on a first area that is a part of the scattering coefficient distribution image,
      identify the first pattern included in the scattering coefficient distribution image,
      identify, as a first area, an area inside of the reference template placed at the relative position with respect to the identified first pattern in the scattering coefficient distribution image, and
      estimate the amount of change in the biological component based on scattering coefficients specified in respective pixels constituting the identified first area in the scattering coefficient distribution image.

2. The apparatus according to claim 1, wherein the processor is further configured to
   project structured illumination having a periodic structure of a given spatial frequency onto the measurement target region,
   photograph the measurement target region to which the structured illumination is projected, so as to acquire a scattered reflection image for light of the structured illumination projected to the measurement target region, and generate the scattering coefficient distribution image from the scattered reflection image, so as to acquire the scattering coefficient distribution image.

3. The apparatus according to claim 1, wherein the processor is further configured to
identify, as the first pattern, a pattern of the biological body stricture included in one of a plurality of such scattering coefficient distribution images,
calculate the reference template in the scattering coefficient distribution image, and calculate a relative position of the placed reference template with respect to the identified first pattern, and
store the identified first pattern and the calculated relative position in the storage unit in a manner associated with the reference template.

4. The apparatus according to claim 1, wherein
the processor is further configured to
acquire an absorption coefficient distribution image having each pixel specified with an absorption coefficient for the light,
identify, as the first pattern, a pattern of the biological body structure included in one of a plurality of such absorption coefficient distribution images,
place the reference template in the absorption coefficient distribution image, and calculate a relative position of the placed reference template with respect to the identified first pattern, and
store the identified first pattern and the calculated relative position in the storage unit in a manner associated with the reference template.

5. The apparatus according to claim 1, wherein the first pattern represents a path of at least one of a blood vessel, a muscle, a tendon, and a ligament included in the biological body.

6. The apparatus according to claim 1, wherein the amount of change in the biological component is an amount of change in a blood glucose level.

7. The apparatus according to claim 1, wherein the processor is further configured to display an image representing the estimated amount of change in the biological component on a display unit.

8. The apparatus according to claim 7, wherein the processor is further configured to display an area representing an abnormal amount of change in the image representing the estimated amount of change in the biological component on the display unit in a display mode that is different from a display mode in which the other area is displayed.

9. The apparatus according to claim 2, wherein the processor is further configured to control outputting of information representing abnormality when an amount of change in the biological component estimated based on the scattering coefficient distribution image generated from a scattered reflection image captured in a predetermined first time period indicates a predetermined abnormal amount of change.

10. The apparatus according to claim 2, wherein the processor is further configured to
detect a positional displacement of the biological component estimating apparatus with respect to the measurement target region; and
display, when the processor has detected a positional displacement, information representing the positional displacement on the display unit.

11. A biological component estimating method comprising:
acquiring a scattering coefficient distribution image having each pixel specified with a scattering coefficient of a measurement target region of a biological body for light including a wavelength range in a near infrared range;
estimating an amount of change in a biological component based on the scattering coefficient distribution image; and
storing a reference template having a size smaller than a size of the scattering coefficient distribution image and also having a predetermined shape, a first pattern of a biological body structure included in the scattering coefficient distribution image, and a relative position of the reference template with respect to the first pattern in the scattering coefficient distribution image, wherein
the estimating of the amount of change in the biological component includes
estimating the amount of change in the biological component based on a first area that is a part of the scattering coefficient distribution image,
identifying the first pattern included in the scattering coefficient distribution image,
identifying, as a first area, an area inside of the reference template placed at the relative position with respect to the identified first pattern in the scattering coefficient distribution image, and
estimating the amount of change in the biological component based on scattering coefficients specified in respective pixels constituting the identified first area in the scattering coefficient distribution image.

12. A computer program product comprising a non-transitory computer-readable medium having programmed instructions stored thereon, the instructions causing a computer to execute:
acquiring a scattering coefficient distribution image having each pixel specified with a scattering coefficient of a measurement target region of a biological body for light including a wavelength range in a near infrared range;
estimating an amount of change in a biological component based on the scattering coefficient distribution image; and
storing a reference template having a size smaller than a size of the scattering coefficient distribution image and also having a predetermined shape, a first pattern of a biological body structure included in the scattering coefficient distribution image, and a relative position of the reference template with respect to the first pattern in the scattering coefficient distribution image, wherein
the estimating of the amount of change in the biological component includes
estimating the amount of change in the biological component based on a first area that is a part of the scattering coefficient distribution image,
identifying the first pattern included in the scattering coefficient distribution image,
identifying, as a first area, an area inside of the reference template placed at the relative position with respect to the identified first pattern in the scattering coefficient distribution image, and
estimating the amount of change in the biological component based on scattering coefficients specified in respective pixels constituting the identified first area in the scattering coefficient distribution image.

* * * * *